(12) United States Patent
Tomcany et al.

(10) Patent No.: US 7,165,278 B2
(45) Date of Patent: *Jan. 23, 2007

(54) PATIENT IMMOBILIZATION DEVICE

(76) Inventors: Brian Tomcany, 19431 Blue Spruce Dr., Strongsville, OH (US) 44149; John A. Helmsderfer, 6909 Kenwood Rd., Cincinnati, OH (US) 45243

( * ) Notice: Subject to any disclaimer, the term of this patent is extended or adjusted under 35 U.S.C. 154(b) by 0 days.

This patent is subject to a terminal disclaimer.

(21) Appl. No.: 11/103,281

(22) Filed: Apr. 11, 2005

(65) Prior Publication Data

US 2005/0229313 A1 Oct. 20, 2005

Related U.S. Application Data

(62) Division of application No. 10/335,523, filed on Dec. 31, 2002, now Pat. No. 7,036,167.

(60) Provisional application No. 60/359,622, filed on Feb. 26, 2002.

(51) Int. Cl.
A61G 1/04 (2006.01)
A61G 1/044 (2006.01)
A61G 1/00 (2006.01)

(52) U.S. Cl. .................. 5/628; 5/622; 5/640
(58) Field of Classification Search ............. 5/628, 5/622, 637, 640, 636, 643, 625, 626, 627; 128/870, 869, 846, 845
See application file for complete search history.

(56) References Cited

U.S. PATENT DOCUMENTS

| 2,377,940 | A | 6/1945 | Hughes | |
|---|---|---|---|---|
| 2,391,928 | A | 1/1946 | Seib | ............... 5/82 |
| 2,394,264 | A | 2/1946 | Robinson | ........... 5/82 |
| 2,511,061 | A | 6/1950 | Hughes | |
| 2,675,564 | A | 4/1954 | Hughes | |

(Continued)

OTHER PUBLICATIONS

Alliance Medical Catalog, *Morrison Medical New & Improved Head Vise™ II Head Immobilizer*, http://www.allmed.net/catalog/showitem.php/3445, Sep. 29, 2002, p.1.

(Continued)

*Primary Examiner*—Alexander Grosz
(74) *Attorney, Agent, or Firm*—Wood, Herron & Evans LLP

(57) ABSTRACT

A patient immobilization device comprises a backboard having a front side and a back side, and a pair of opposing paddles slidably mounted on the backboard. The paddles are configured to move between a storage position and a support position, to support the head of a patient. Each paddle has a leg portion depending therefrom and extends through a respective slot formed in the backboard between the front and back and sides. A spanning portion of the paddle depends from the leg portion and engages the back side of the backboard to secure the paddle to the backboard. The spanning portion moves in a generally arcuate path between the storage and support positions. In one embodiment, the paddles are flexible along their height so that a portion of the paddle can flex to rotate under the force of a securing structure. In another embodiment, the paddles have multiple sections, with one of the sections being movable to a storage position to expose a portion of the head or neck of a user.

5 Claims, 11 Drawing Sheets

U.S. PATENT DOCUMENTS

| | | | | |
|---|---|---|---|---|
| 2,770,465 | A | 11/1956 | Dandurand | 280/12 |
| 3,222,080 | A | 12/1965 | Kinraide | 280/18 |
| 3,449,776 | A | 6/1969 | Brock | 5/627 |
| 3,650,523 | A | 3/1972 | Darby, Jr. | 5/603 |
| 3,653,079 | A | 4/1972 | Bourgraf et al. | 5/82 |
| 3,689,945 | A | 9/1972 | Laerdal | 5/82 |
| 3,707,734 | A | 1/1973 | Matthews | 5/82 |
| 3,737,923 | A | 6/1973 | Prolo | 5/82 |
| 3,775,782 | A | 12/1973 | Rice et al. | 5/82 |
| 3,890,659 | A | 6/1975 | Staubs | 5/82 |
| 4,024,861 | A | 5/1977 | Vincent | 128/87 |
| 4,033,000 | A | 7/1977 | Bonifay | 5/82 |
| 4,064,574 | A | 12/1977 | Schnitzler | 5/82 |
| 4,124,908 | A | 11/1978 | Burns et al. | 5/82 |
| 4,252,113 | A | 2/1981 | Scire | 5/628 |
| 4,267,830 | A | 5/1981 | Vick | 128/87 |
| 4,347,635 | A | 9/1982 | Eisenhauer | 441/40 |
| 4,369,982 | A | 1/1983 | Hein et al. | 280/47.13 |
| 4,480,345 | A | 11/1984 | Dunn | 5/82 |
| 4,571,757 | A | 2/1986 | Zolecki | 5/628 |
| 4,771,493 | A | 9/1988 | Park | |
| 4,794,656 | A | 1/1989 | Henley, Jr. | 5/82 |
| 4,928,711 | A | 5/1990 | Williams | 128/869 |
| 5,201,089 | A | 4/1993 | Ferreira | 5/627 |
| 5,211,185 | A | 5/1993 | Garth et al. | 128/870 |
| 5,265,625 | A | 11/1993 | Bodnia | 128/869 |
| 5,395,158 | A | 3/1995 | Cordia | 297/393 |
| 5,414,883 | A | 5/1995 | Fangrow, Jr. | 5/625 |
| 5,473,784 | A * | 12/1995 | Nixon et al. | 5/625 |
| D367,834 | S | 3/1996 | Beavers et al. | D12/133 |
| 5,657,766 | A | 8/1997 | Durham | 128/870 |
| 5,729,850 | A | 3/1998 | Eskeli | 5/621 |
| D403,423 | S | 12/1998 | Bologovsky et al. | D24/190 |
| 5,944,016 | A | 8/1999 | Ferko, III | 128/869 |
| 5,950,627 | A | 9/1999 | Bologovsky et al. | 128/869 |
| D425,992 | S | 5/2000 | Davis et al. | D24/189 |
| 6,170,486 | B1 | 1/2001 | Islava | 128/869 |
| 6,244,270 | B1 | 6/2001 | Lutian et al. | 128/869 |
| 6,327,723 | B1 | 12/2001 | Knight | 5/628 |
| D462,448 | S | 9/2002 | Huttner | D24/191 |
| 6,443,157 | B1 | 9/2002 | Sargent | 128/870 |
| D469,541 | S | 1/2003 | Cheatham | D24/191 |
| 6,637,057 | B2 | 10/2003 | Phillips et al. | |
| 6,659,104 | B2 | 12/2003 | Kiefer et al. | 128/870 |
| 6,862,759 | B2 | 3/2005 | Hand et al. | 5/430 |
| 2004/0016057 | A1 | 1/2004 | Traut et al. | |
| 2004/0049852 | A1 | 3/2004 | Phillips et al. | |

OTHER PUBLICATIONS

Alliance Medical Catalog, *Laerdal® BaXstrap® Spineboard*, http://www.allmed.net/catalog.showitem.php/3454, Sep. 29, 2002, p. 1.

Alliance Medical Catalog, *Allied LSP HDx® Backboard*, http://www.allmed.net/catalog/showitem.php/3453, Sep. 29, 2002, pp. 1-2.

Alliance Medical Catalog, *Dispos-A-Board® Backboard*, http://www.allmed.net/catalog/showitem.php/3463, Sep. 29, 2002, pp. 1-2.

Alliance Medcal Catalog, *Bashaw Rough Terrain CID*, http://www.allmed.net/catalog/showitem.php/3434, Sep. 29, 2002, p. 1.

Alliance Medical Catalog, *Allied LSP SpineX® Backboard*, http://www.allmed.net/catalog/showitem.php/3449, Sep. 29, 2002, p. 1.

Alliance Medical Catalog, *Allied LSP Stabilizer® Backboard*, http://www.allmed.net/catalog/showitem.php/3450, Sep. 29, 2002, p. 1.

Alliance Medical Catalog, *I-Tec® Multi-Grip Head Immobilizer*, http://www.allmed.net/catlog/showitem.php/3438, Sep. 29, 2002, p. 1.

Alliance Medical Catalog, *EP&R Bak-Pak*, http://www.allmed.net/catalog/showitem.php/4115, Sep. 29, 2002, p. 1.

Alliance Medical Catalog, *Morrison Medical Sticky Blocks™ Head Immobilizers*, http://www.allmed.net/catalog/showitem.php/4396, Sep. 29, 2002, p. 1.

Alliance Medical Catalog, *Morrison Medical Head Vise™ I Reusable Head Immobilizer*, http://www.allmed.net/catalog/showitem.php/3444, Sep. 29, 2002, p. 1.

Alliance Medical Catalog, *Bashaw Infant CID*, http://www.allmed.net/catalog/showitem.php/4124, Sep. 29, 2002, pp. 1-2.

Alliance Medical Catalog, *Morrison Medical Head Blocks?™ Set, With Straps*, http://www.allmed.net/catalog/showitem.php/4401, Sep. 29, 2002, pp. 1-2.

Alliance Medical Catalog, *Morrison Medical Head Vise™ III*, http://www.allmed.net/catalog/showitem.php/4410, Sep. 29, 2002, p. 1.

Alliance Medical Catalog, *Morrison Medical Head Blocks™, Disposable Foam*, http://www.allmed.net/catalog/showitem.php/4398, Sep. 29, 2002, p. 1.

Alliance Medical Catalog, *Laerdal® HeadBed® II Head Immobilization Device*, http://www.allmed.net/catalog/showitem.php/3432, Sep. 29, 2002, p. 1.

Alliance Medical Catalog, *Laerdal® Speedblocks® Head Immobilizer*, http://www.allmed.net/catalog/showitem.php/3431, Sep. 29, 2002, pp. 1.

Alliance Medical Catalog, *STI Sta-BLok™ Head Immobilizer*, http://www.allmed.net/catalog/showitem.php/3446, Sep. 29, 2002, p. 1.

Pro-Lite Spineboard, *Pro-Lite Spineboard®*, http://www.allmed.net/catalog/showitem.php/3448, Sep. 29, 2002, p. 1.

Dispos-O-Bag, *Dispos-O-Bag® Head-On® Block*, http://www.allmed.net/catalog/showitem/php/3441, Sep. 29, 2002, p. 1.

Pro-Lite XT, *Pro-Lite XT®*, http://www.allmed.net/catalog/showitem.php/3447, Sep. 29, 2002, pp. 1-2.

Bound Tree, *Hoover Headblock*, http://www.boundtree.com/quickdet., Sep. 29, 2002, p. 1.

Brittany Board, *Brittany Board*, http://www.brittanyboard.com/home.html, Sep. 29, 2002, p. 1.

Ferno, *Model 455 HeadHugger™ Disposable Head Immobilizer*, http://emergency.ferno.com/immobilize/model455.htm, Sep. 29, 2002, p. 1.

Ferno, *Model 445 Universal Head Immobilizrt*, http://emergency.ferno.com/immobilize/model445.htm, Sep. 29, 2002, p. 1.

Ferno, *740/750 Series Phenolic Wooden Backboards* http://emergency.ferno.com/immobilie/model_740_750.htm, Sep. 29, 2002, p. 1.

Iron Duck Catalog, *Ultra Loc Backboard & Head Loc II*, http://www.ironduck.com/catalog.epl?ProducID=118, Sep. 29, 2002, pp. 1-4.

Junkin Safety Appliance Company, *Junkin Safety Backboards*, http://www.junkinsafety.com/products/backbrd.html, Sep. 29, 2002, pp. 1-2.

Ferno, *Millenia™ Plastic Backboards*, http://emergency.ferno.com/immobilize/bckbrds.htm, Sep. 29, 2002, p. 1.

Morrison Medical, *Morrison Medical—Head Immobilzers*, http://mossisonmed.com/head.htm, Sep. 29, 2002, pp. 1-2.

NAJO™ Backboards, *NAJO™ Backboards*, http://reefmedical.com./au/najo, Sep. 29, 2002, pp. 1-3.

PMX, *PMX Backboard*, http://www.pmxmedical.com/catalog/page30.html, Sep. 29, 2002, p. 1.

Reefmedical, *Ambu® NAJO™ Head Wedge*, http://reefmedical.com.au/headwedge.htm, Sep. 29, 2002, pp. 1-2.

Reeves, *The Reeves Sleeve®*, http://www.reevesdecon.com/sleeve.htm, Sep. 29, 2002, p. 1.

Reeves, *Reeves® Spine Board*, http://www.pmxmedical.com/catalog/page30.html, Sep. 29, 2002, p. 1.

* cited by examiner

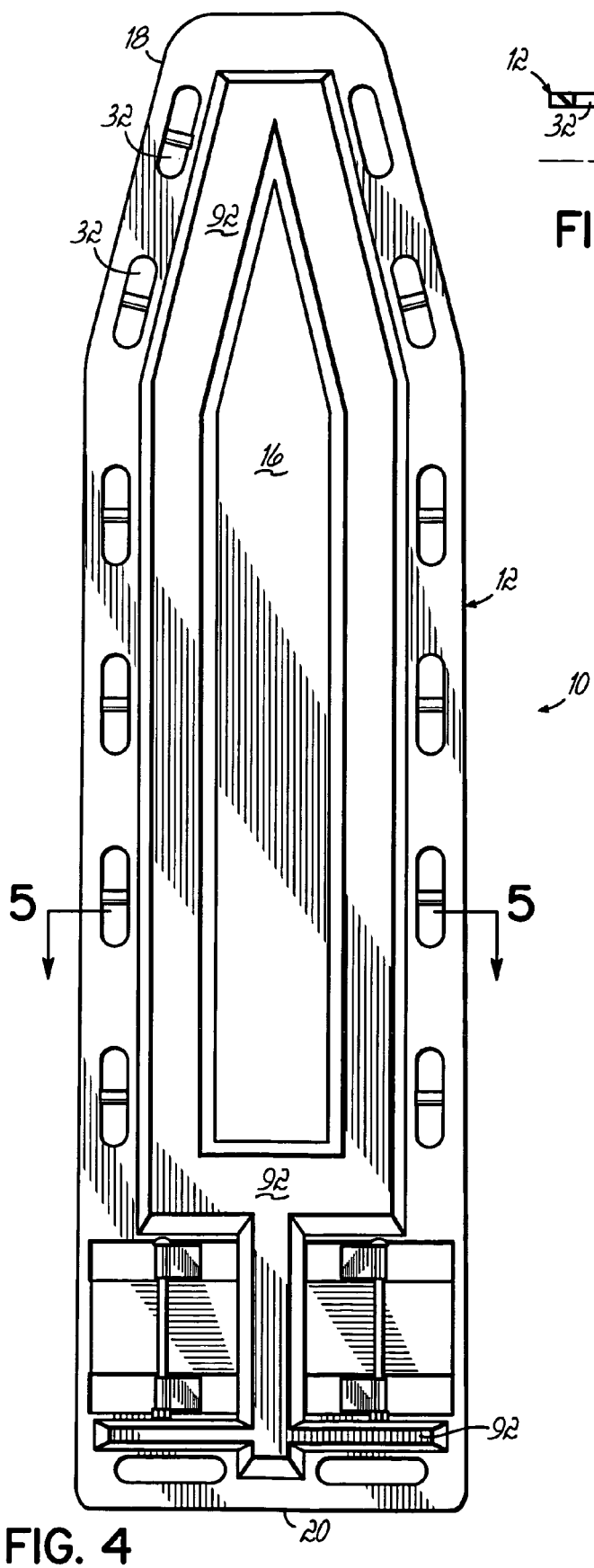
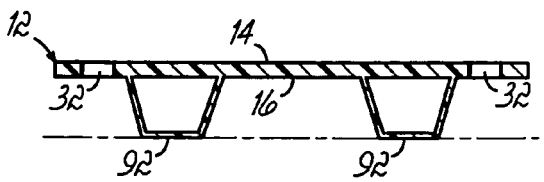
FIG. 5
FIG. 4

PATIENT IMMOBILIZATION DEVICE

RELATED APPLICATION

This application is a divisional patent application of, and claims priority to, U.S. patent application Ser. No. 10/335,523 filed Dec. 31, 2002, now U.S. Pat. No. 7,036,167 and entitled "Patent Immobilization Device," which application claims priority to Provisional Application Ser. No. 60/359,622, filed Feb. 26, 2002, and entitled "Backboard with Head Immobilizer," which applications are all incorporated herein by reference in their entireties.

FIELD OF THE INVENTION

This invention relates generally to a patient immobilization device including a backboard and head immobilizer used to support and immobilize injured patients.

BACKGROUND OF THE INVENTION

In accidents involving apparent injury to the head, neck, and/or spine, the patient is immobilized for treatment and transport. Specifically, the head and cervical spine areas of the patient are routinely immobilized to prevent further injury during transport to a medical facility. For such immobilization, devices such as rigid backboards are typically used to support and assist in immobilizing the patient during this time. A head immobilization device or immobilizer is used with the backboard. For example, the patient is placed on a board and stiff pillows or blocks are placed tightly on either side of his head. A combination of headstraps, chin-straps, and tapes are then tightly secured over the pillows/blocks and the board to fixedly hold the patient's head in place on the board.

Currently, there are several typical types of head immobilizers in use that are incorporated generally with a flat backboard. One type of head immobilization system utilizes a pair of reusable blocks, which are formed of a pliant, yet supportive material such as rigid foam or a suitable vinyl material. Generally, such blocks are secured to a board with hook and loop fastening structures, such as Velcro™.

Another type of immobilizer is disposable and utilizes inexpensive cardboard, which is manipulated to form a support structure for the head and neck. Generally, such a cardboard material is temporarily coupled to a backboard with an adhesive material. Other types of head immobilization systems utilize a combination of reusable and disposable elements that may be temporarily coupled to a backboard.

Although such systems have proven suitable for use with a backboard to immobilize a patient, they present other problems. While reusable foam or vinyl blocks may be relatively inexpensive, due to reuse, they must be repeatedly cleaned and maintained after each use to prevent the transmission of unsafe pathogens, either through blood or other bodily fluid, such as vomit. Repeated cleaning of the blocks may cause premature deterioration of the blocks and their covering or outer skin. Also, foam material can effectively turn into a sponge, thus trapping blood-borne pathogens and other pathogens. As such, after a certain amount of use, even reusable blocks will need to be replaced.

Another problem with such reusable blocks is that they are difficult to store when not in use. Emergency medical vehicles provide little excess storage space for equipment and materials. Therefore, generally, the reusable blocks are stored in a location that is remote from the tall narrow opening provided for backboard storage, such as in an ambulance. Separation of key pieces of the patient immobilization equipment for the purpose of storage can often lead to lost or misplaced items. This is particularly critical at an accident or medical emergency when the retrieval time may be critical for the patient's health and well being. Accident scenes are often chaotic environments involving multiple emergency medical service providers. Therefore, any lost time involved in gathering up all the pieces necessary for head and neck support and patient immobilization is particularly undesirable.

Furthermore, because the blocks are separate pieces from the board, they often become lost or are mistakenly collected by other medical providers, such as at an accident scene or during equipment recollection at a medical facility. As may be appreciated, patients may come into a hospital emergency room, supported and immobilized on the equipment of several rescue teams. The rescue teams then return to the scene of the accident for other patients or victims, or go out on other calls, and they leave the equipment at the hospital with their patients. After the equipment is removed, it is often placed in a common area for the various teams to recover. During such recovery, one team or unit may inadvertently grab the equipment of another unit.

Single-use, disposable head immobilization devices and systems do have some advantages over reusable systems in that they are generally smaller, are easier to store in an ambulance, and do not have to be recovered because they are discarded after one use. Furthermore, since they are not reused, they do not have to be cleaned and they do not present a significant risk with respect to transmission of unsafe bodily fluids from one patient to the next. However, because they are single-use devices, an emergency medical service provider must purchase and store a sufficient amount so as not to run out during response to an emergency situation. This requires frequent purchases, control of inventory at a central storage area, and distribution of the devices to all the vehicles that would use the devices. This essentially increases the overall cost of the equipment for an emergency service provider.

Furthermore, because such single-use devices often utilize adhesives for attachment to a backboard, repeated attachments require the removal and cleaning of the board proximate the adhesive. Repeated cleaning of the adhesive portions of the device after each use becomes a nuisance for the user.

Another drawback with disposal head immobilization devices is that they often use cardboard as their primary construction material. Many patients and the public, in general, do not perceive cardboard as a particularly robust material as compared with other materials used to make emergency medical equipment, such as rigid plastic used to make backboards and cervical collars. Patient and public perception of high quality care and equipment materials is an important factor in providing satisfactory service from emergency medical providers. Notwithstanding perception, the robustness of the devices themselves is important. Some patients may require intubation tubes to assist with breathing. Intubated patients who dislodge their tubes would have to be immediately attended to in order to maintain an unobstructed airway. One prevalent cause of a dislodged intubation tube is movement, particularly head movement, which can occur when a patient is panicking or is having a seizure. Therefore, it is important to have robust head immobilization devices that are sufficiently coupled with the backboard in order to keep patients from dislodging their intubation tubes.

Therefore, there exists a need for a patient immobilization device which addresses these issues. The present invention addresses various of the above drawbacks in the prior art and provides other advantages to assist in the care of patients requiring head and neck immobilization.

SUMMARY OF THE INVENTION

The patient immobilization device, the present invention, comprises a backboard having a front side and a back side. Generally, the patient is placed on the front side while the back side rests against a surface, such as the ground. A pair of opposing paddles are slidably mounted on the backboard and are configured to move between a storage position up against the backboard in a support position where they support the head and neck of a patient lying on the backboard. Each paddle has a leg portion depending therefrom and extending through a respective slot formed in the backboard between the front and back sides. Securing the paddle with the backboard is a spanning portion that depends from the leg portion and engages the back side of the backboard. When the paddle is moved between the storage position and the support position, the spanning portion moves in a generally arcuate path. In that way, while the paddle is held in place in the storage and support positions, it is freely movable between those positions, as the spanning portion moves in an arcuate path away from the backboard.

In one embodiment of the invention, index structures are utilized to secure the paddles into place in the support position. The index structure may be positioned on a front or a back side of the backboard. On the front side of the backboard, the index structure is engaged by the body of the paddle. On the back side of the backboard, the index structure may be engaged by the spanning portion of the paddle. In one embodiment, the spanning portion is a dowel that extends outwardly from a leg portion or between multiple leg portions. The paddle or spanning portion engages an index structure in the form of a plurality of grooves. Preferably, the grooves are open-ended and open into slots formed through the backboard so that the grooves may be easily cleaned and do not trap blood or other debris.

In an alternative embodiment of the invention, a friction engagement of the paddle and the backboard, rather than an index structure, ensures that the paddle is locked and placed into the support position. In one embodiment, a cam structure is coupled with a leg portion of the paddle and engages the back side of the backboard when the paddle is moved to the support position to secure the paddle into place. When the paddle is moved between the storage position and the support position, the cam structure is disengaged and the paddle may be slid to the desired position on the backboard to accommodate the width of the patient's head.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 4 is a bottom plan view of one embodiment of the backboard of the present invention.

FIG. 5 is a cross-sectional view along lines 5—5 of FIG. 4.

FIG. 20 is an end cross-sectional view of another embodiment of the present invention.

DETAILED DESCRIPTION OF SPECIFIC EMBODIMENTS OF THE INVENTION

Figure 1:
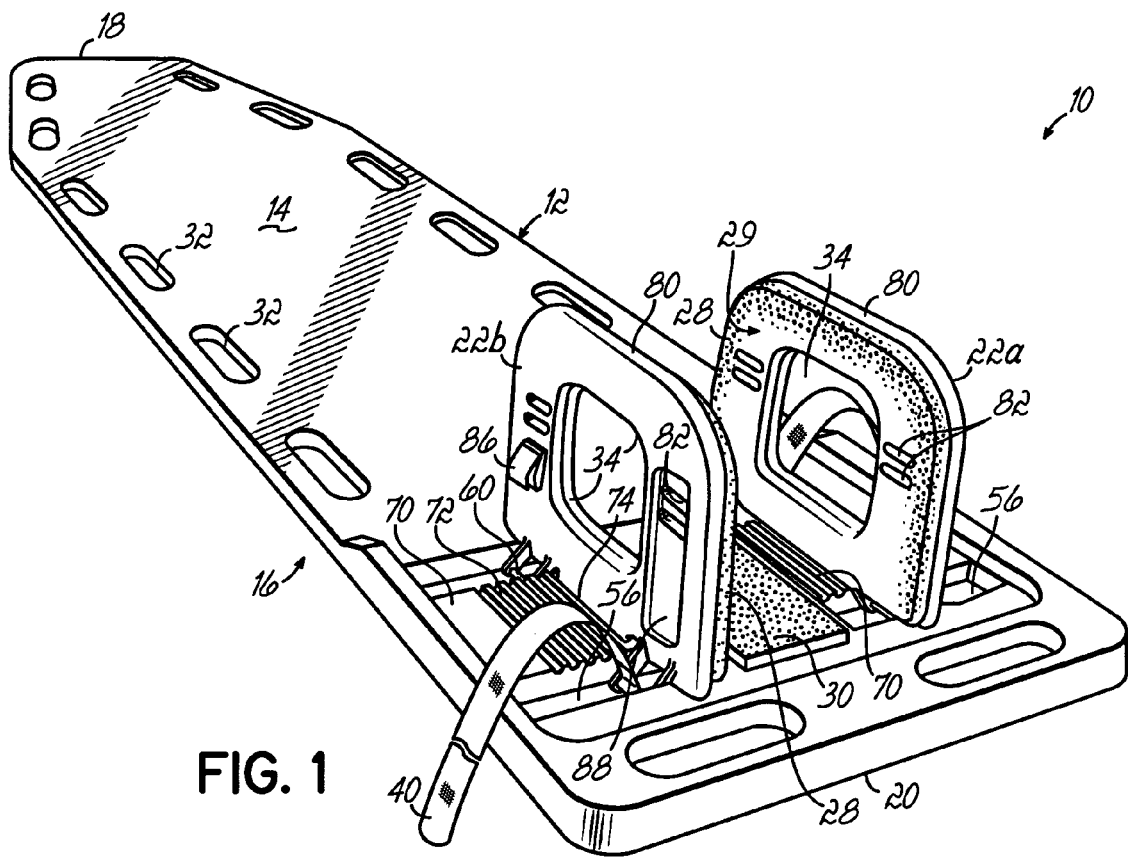
FIG. 1 is a perspective view of one embodiment of the present invention.

Referring to FIG. 1, a perspective view of a patient immobilization device 10 of the invention is illustrated. Generally, such a device comprises a backboard or backboard portion 12, having a top side or front side 14, and a bottom side or back side 16. In use, a patient would generally be placed on the front side 14, with their feet at the foot end 18 of the backboard and their head at the head end 20 of the backboard. For securing the head and neck of a patient, the invention utilizes a pair of opposing paddles 22a and 22b, which are slidably mounted on the backboard 12, and are configured, in a support position, to support the head and neck of a patient. Embodiments of the paddles 22a, 22b are illustrated in the support position in FIG. 1.

Figure 1A:
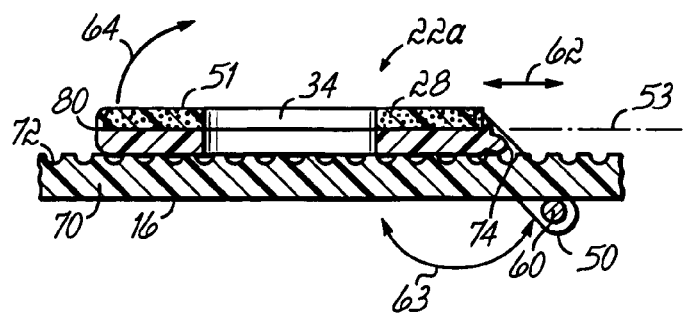
FIG. 1A is a side view, in cross-section, of a paddle of the present invention, in a storage position.
Figure 1B:
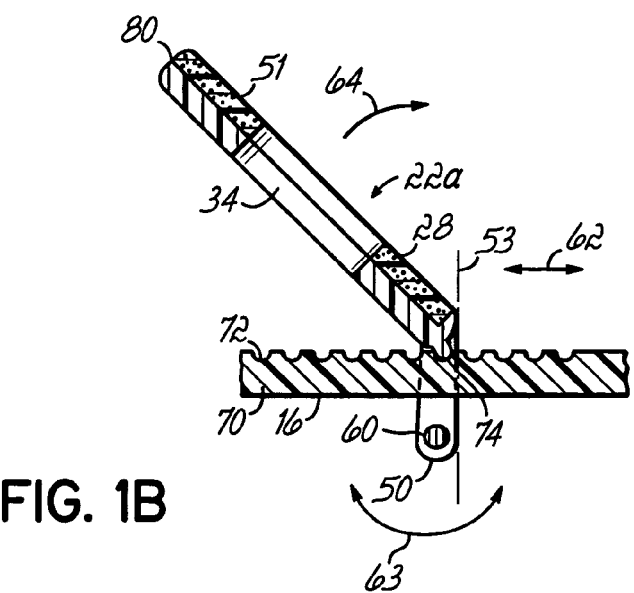
FIG. 1B is a side view, similar to FIG. a!., of a paddle moving between a storage position and a support position.
Figure 2O:
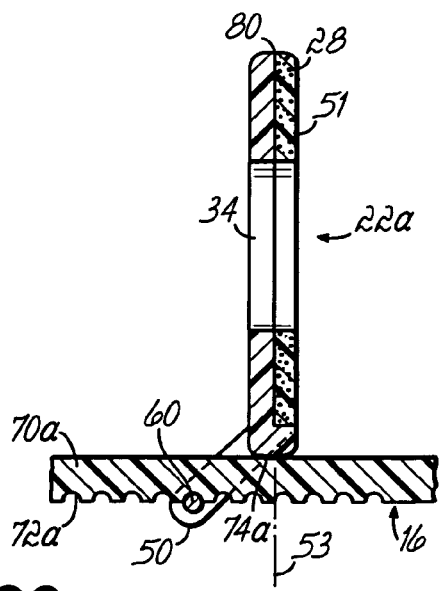
FIG. 2 is a partial perspective view of one embodiment of the invention illustrating an immobilized patient.
Figure 2:
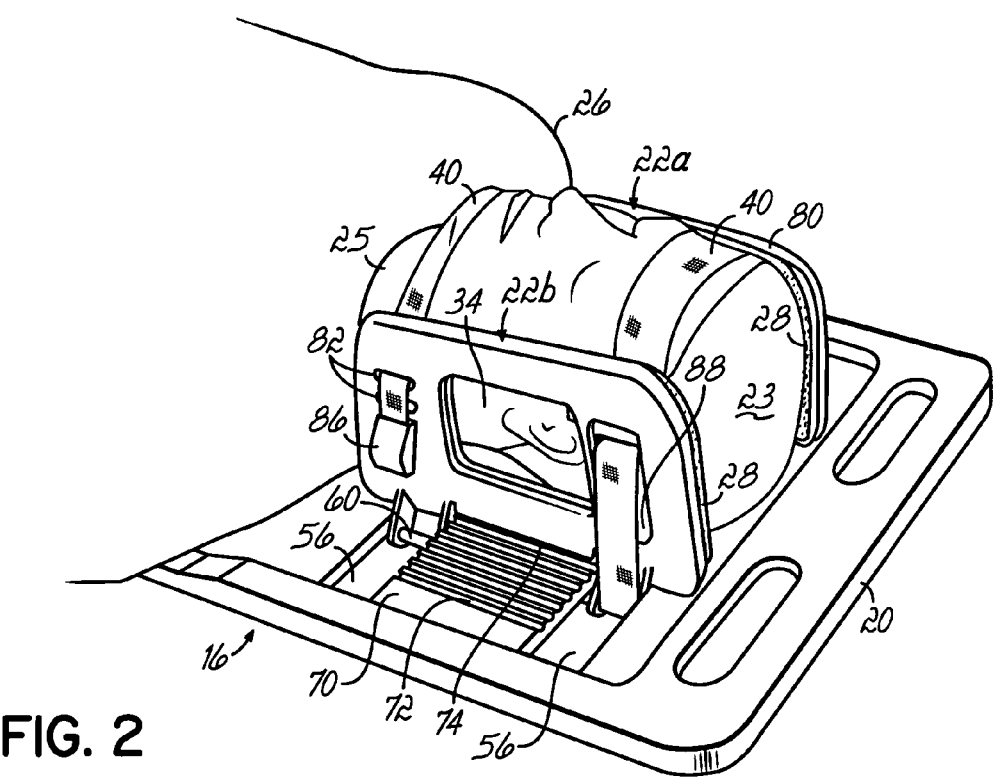
Figure 7:
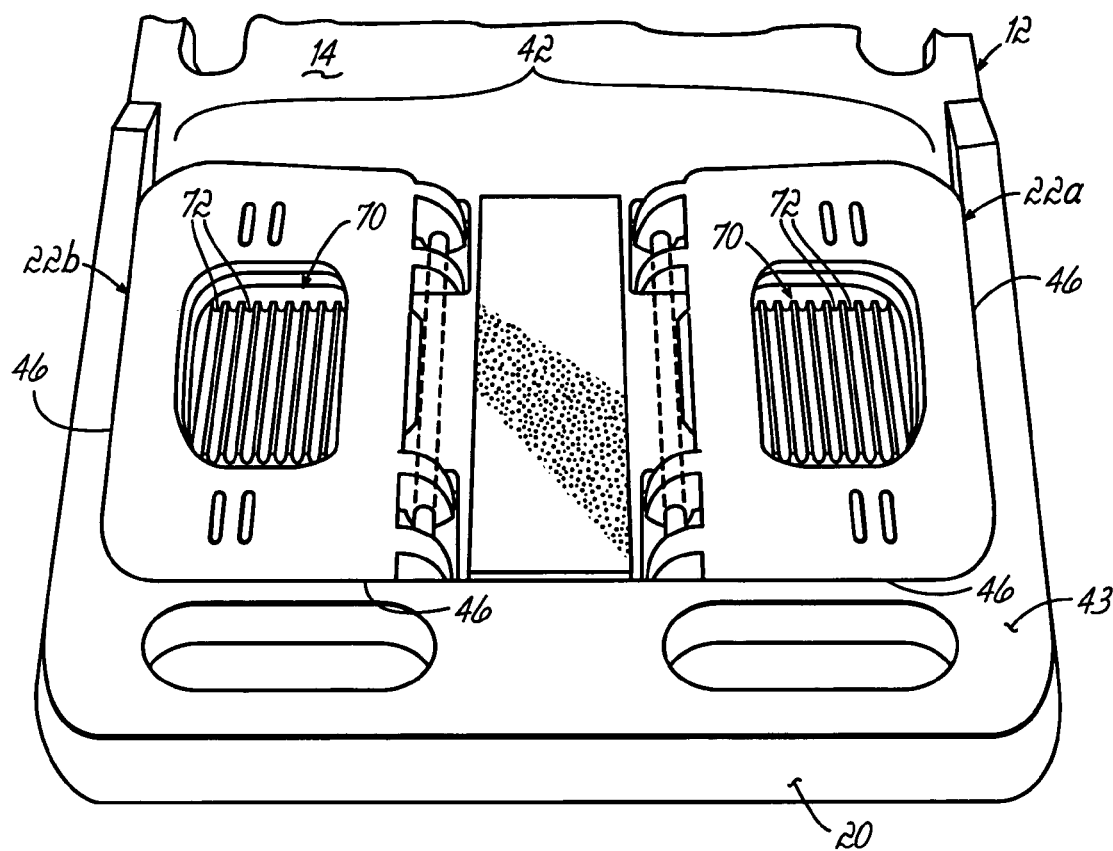
FIG. 7 is a perspective view of an embodiment of the invention illustrating paddles in the storage position.

Referring to FIG. 2, the head 23 and neck 25 of the patient 26 are secured and immobilized between the paddles during use. The body of the patient 26 lies along the length of the backboard 12, and often is secured to the backboard with straps, tape or other securement structures (not shown). As illustrated in FIGS. 1A, 1B, and 7, and discussed herein below, the paddles are movable between a support position or upright position, as illustrated in FIG. 1, and a storage position or flat position (see FIG. 7) for storing the device 10 when not in use.

The backboard 12 can be made out of wood, plastic, or any other suitable, and preferably light weight, material for supporting a patient with their head and neck immobilized between the paddles 22a, 22b.

The paddles may be made of a suitable rigid and light weight material, such as wood or plastic. For example, a polypropylene plastic, or high density polyethylene (HDPE) might be suitable. Paddles 22a, 22b include a layer or portion 28 of a conformable material for providing cushioning and comfort to the head 23 of the patient while providing a level of conformability to the paddles, for better securement and immobilization of the head and neck. For example, the layer 28 might be made of a conventional foam, such as a polyurethane foam, covered in a protective skin for cleanability. The protective skin 29 on the foam 28 provides an impermeable membrane for resisting the collection of bodily fluids and bacteria. Such a foam material is desirable both for its durability and its resistance to extreme temperatures and harsh chemicals, such as disinfectants.

To provide further comfort for an immobilized patient, a cushion 30 or a cushioned area between the paddles 22a, 22b might be used for cushioning the back of the head 23 of the patient. When a patient 26 is secured with the inventive device 10, as illustrated in FIG. 2, the backboard 12 may then be lifted utilizing hand holes 32, as are conventional with backboards.

Figure 3:
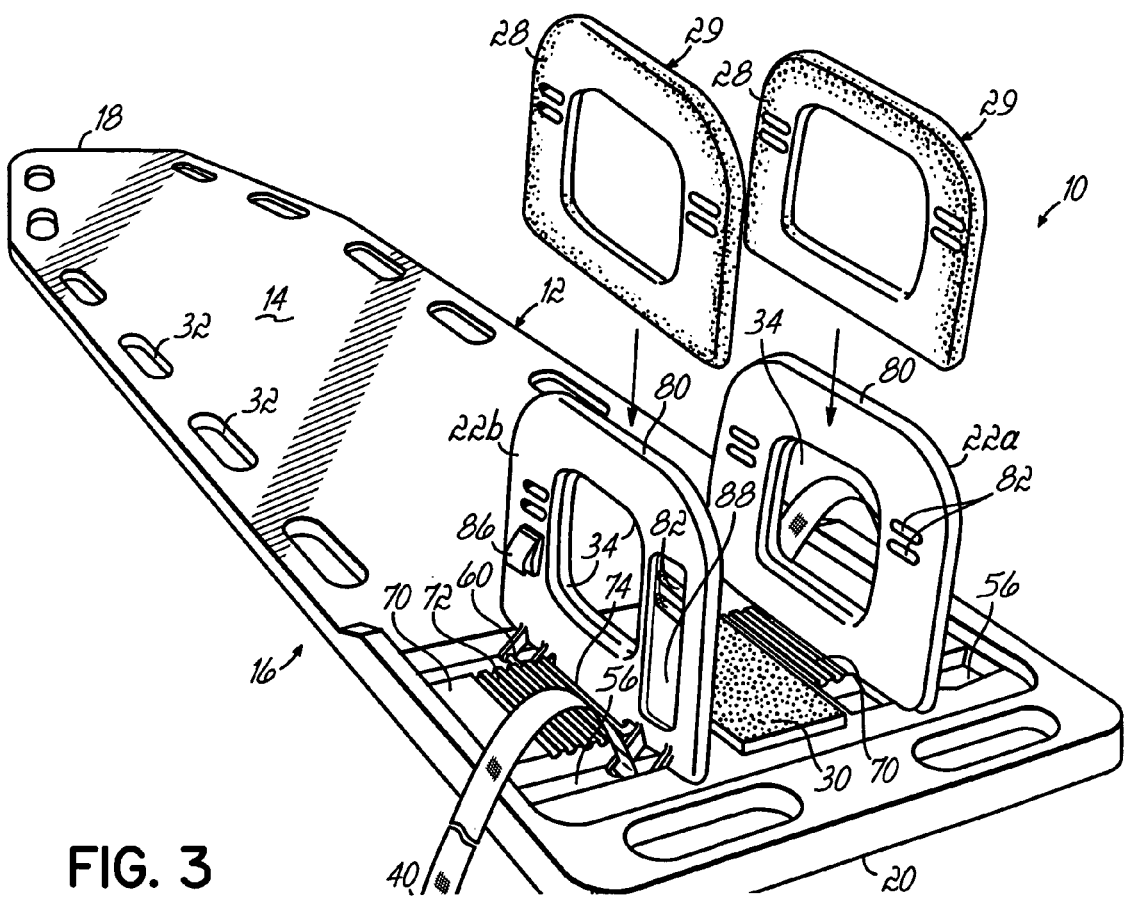
FIG. 3 is a perspective view of an alternative embodiment of the present invention.

Referring to FIG. 3, the layer 28 or layer material, may be removable, such as for cleaning purposes. For example, the cushions 23 might be held to the paddles 22a, 22b by a suitable adhesive, by hook/loop fasteners, or by physically sliding the layers into tracks (not shown) formed within the paddles. Other suitable securement methods may also be utilized to removably secure the layers 28 with the paddles 22a, 22b. Preferably, the material utilized to form the paddles and any conformable layers 28 herewith is x-ray translucent so that x-rays may be taken with the patient in a stabilized position, as illustrated in FIG. 2.

The paddles 22a, 22b and associated conformable layers 28 have openings 34 formed therein so that the patient may hear better, such as for hearing instructions from a care giver or emergency medical personnel. Often overlooked during patient transport is the patient's ability to hear. The ear holes 34 are free from obstructions, thus decreasing the possibility of miscommunication with an injured patient.

Furthermore, the openings 34 allow visual inspection of the ears, or fluid coming from the ears, which is often indicative of head trauma. The ear holes, or openings 34, are placed to allow for greater visualization of a patient's ear. Ear holes 34 allow for better visualization and touch by medical personnel. In that way, they provide important diagnostic information about the type and extent of the injury by the type and amount of any fluid drainage of the ear. In one embodiment, the ear openings or ear holes 34 have an aspect ratio (i.e., the ratio of the depth or thickness of the paddle at opening 34 to the width or length of the opening 34), conducive to better hearing.

Figure 13:
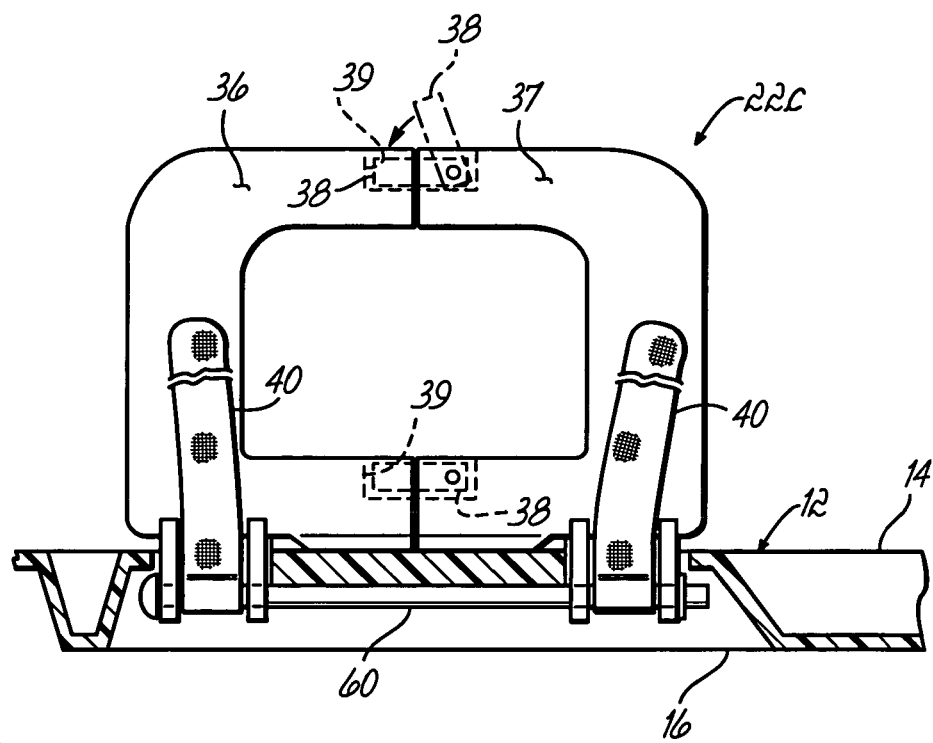
FIG. 13 is a side view, in partial cross-section, of another alternative paddle of the present invention.
Figure 14:
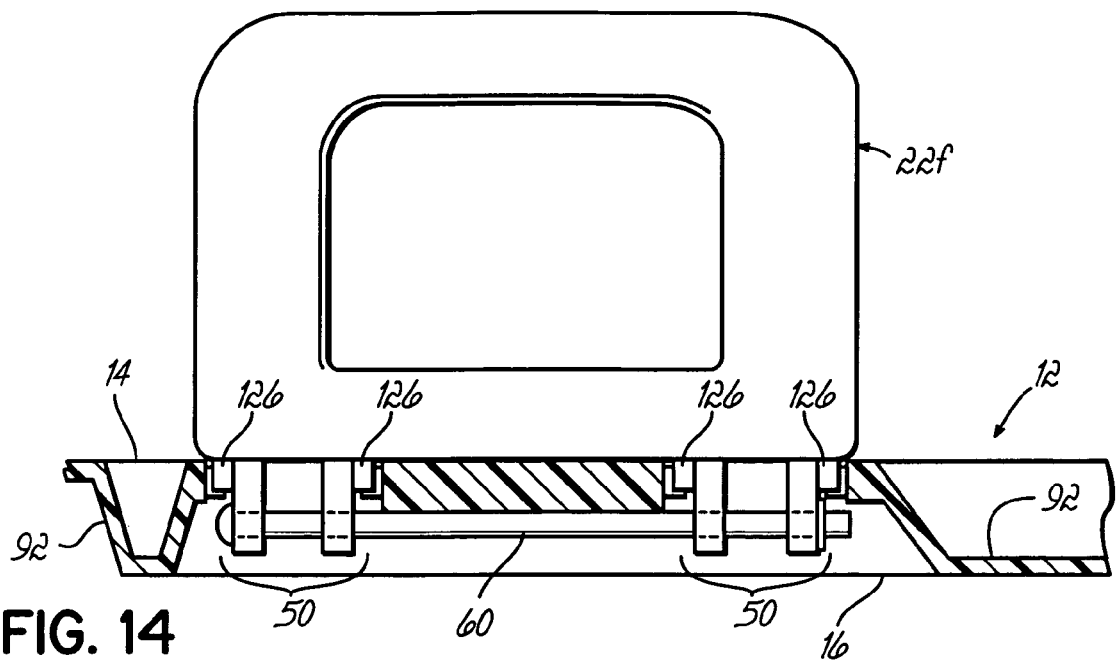
FIG. 14 is a side view, in partial cross-section, of an alternative embodiment of the present invention.
Figure 15:
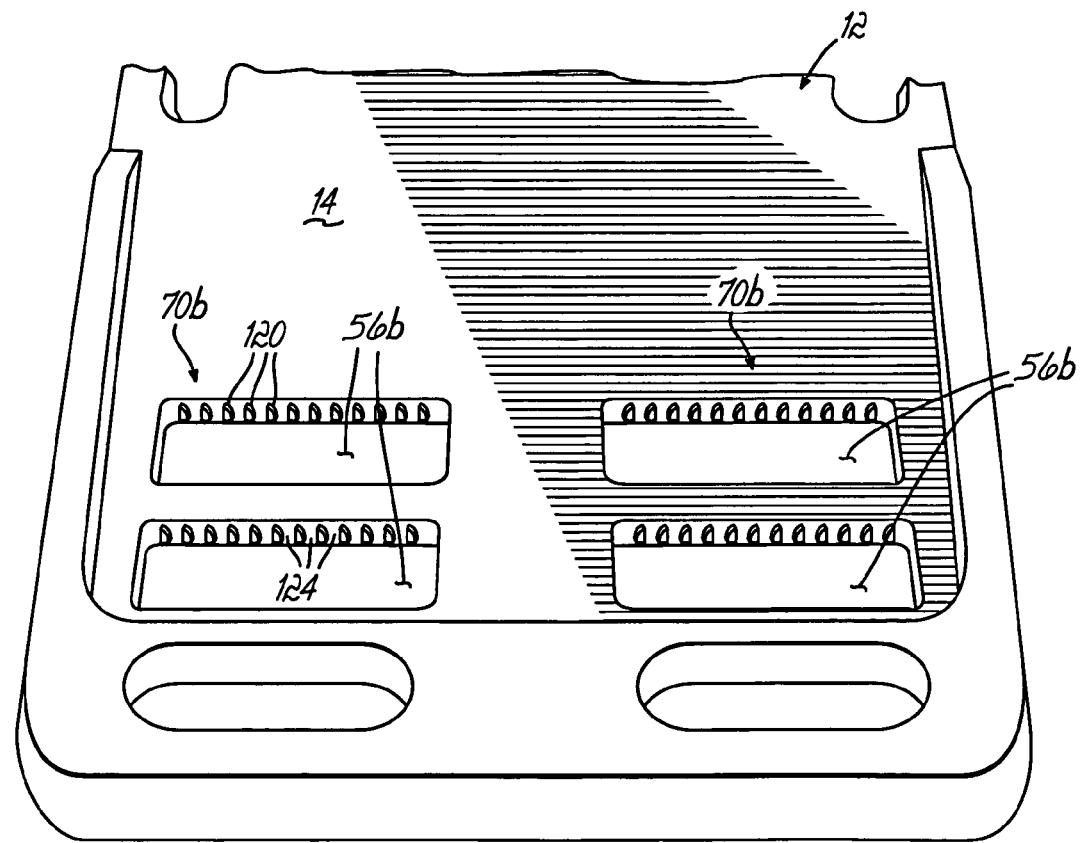
FIG. 15 is a perspective view of an alternative embodiment of the present invention, with the exemplary paddles removed for clarity.

In an alternative embodiment of the paddles, as illustrated in FIG. 13, the paddle might be split into multiple sections for visual and manual examination. One section is movable to a storage position to expose a portion of the head and/or neck while the other section remains in a support position to support the head and/or neck. Paddle 22c, FIG. 13, includes two sections: 36 and 37, which may be coupled together with a coupling structure such as a clasp, key, or other structure. For example, in FIG. 13, rotatable keys 38 are shown that rotate into appropriately formed key slots 39, formed in sections 36, 37. The keys 38 in slots 39 assure that the paddle sections stay together to form the unitary paddle 22c for immobilizing the head and neck of a patient. When it is desirable to physically examine the neck or part of the head, the appropriate section of paddles 22c may be uncoupled and folded to a storage position to allow access to a portion of the head or neck. The other section remains in the support position to continue to support the head and neck. Then, the section can be folded back up into a support position, and secured to form a unitary paddle 22c.

The shapes of the paddles, which are shown generally in a side view to resemble the shape of a "D" or "O", provides support for both the temporal and parietal areas of the skull, while also providing support for the zygomatic arch and any cervical collar utilized on the patient, as illustrated in FIG. 2. To secure the patient's head and neck between the paddles and to hold the paddles in a support position against the head and neck of the patient, one or more straps 40 or other securement structures are utilized. The straps span between the paddles, as illustrated in FIG. 2 and hold them in the support position. In accordance with one aspect of the invention, the straps 40 are integral with the device 10 and remain with it even when stored. In that way, the necessary straps are always with the device and do not have to be separately stored and retrieved. In the embodiment shown in FIGS. 1 and 2, one end of the straps is secured to the device 10, while a free end may be spanned between the paddles, based upon the width of the patient's head and the separation of the paddles. Securement, adjustability, and storage of such straps 40 are discussed herein below, in accordance with other aspects of the invention. Also, as noted below, other securement structures (i.e., tape, separate straps) might be utilized.

In accordance with one aspect of the present invention, the paddles 22a, 22b are secured to the backboard 12, and remain with the device 10 not only when in use, but also when it is stored. To that end, the paddles are movable from a support position, as illustrated in FIGS. 1 and 2, to a storage position, as illustrated in FIGS. 1A and 7. In one embodiment of the invention, the paddles are essentially rotatably mounted with respect to the backboard, and rotate between the storage positions and support about axes, which are generally parallel with the longitudinal axis of the backboard. Referring to FIGS. 1A, 1B, and 1C, the rotation of the paddles in one embodiment is illustrated. As discussed below, portions of the paddles, which extend through the board and along the back side, travel in a generally arcuate path between the storage and the support position. Referring to FIG. 7, in one aspect of the invention, the backboard, proximate the head end 20, forms a recess 42 to receive the paddles 22a, 22b in the storage position so that the paddles are generally flush with or below the front side surface 43 of the backboard proximate the head end 20. As is illustrated in FIG. 7, a raised area of the backboard is formed proximate to the head end to create such a recess to receive the stored paddles. Alternatively, the backboard 12 might be molded so as to form indents into the board to receive the paddles. For example, the entire thickness of the backboard might match that shown at the head end in the embodiment illustrated in FIGS. 1, 2, and 7 with a recessed area 42 formed therein for the paddles. The paddles 22a, 22b and the recessed area 42 may be appropriately configured and dimensioned to provide an interference fit for the paddles to keep them in the storage position until needed for use. For example, an interference or friction fit at the edges 46 of the paddle might keep them in the recessed area 42 until they are pulled upwardly to a storage position. Alternatively, some kind of latching or securement mechanism might be used to keep the paddles in place.

In accordance with another aspect of the present invention, the opposing paddles 22a, 22b are also slidably mounted with respect to the backboard to adjust their positions on the backboard. When the paddles are pulled up from the storage position and toward the support position, they may then be freely slid toward each other or apart to adjust to the width of the patient's head, neck, or any other medical gear or items attached thereto. Generally, in the storage position, the paddles are at 0 degrees with respect to the front side 14 of the backboard, or with respect to the overall plane of the backboard. In the support position, as illustrated in FIGS. 1 and 2, the paddles are approximately generally perpendicular to the front side 14 or to the plane of the backboard 12. Of course, the paddles may be angled somewhat from a perpendicular position, and it is not critical that they are at 90 degrees with respect to the plane of the backboard in the support position. In accordance with an aspect of the invention, the paddles are configured so that generally when they are oriented at an angle between the range of approximately 20 degrees to 70 degrees from the plane of the backboard, they may be slid freely together and apart for proper adjustment. Of course, angled outside this range, they may slide as well, just not as freely. Once in the support position or perpendicular position, they engage a respective index structure, as discussed herein below, to lock the paddles at a desired separation for support of the patient's head 23 and neck 25 as illustrated in FIG. 2.

Turning now to FIGS. 1A, 1B and 1C, the paddles include one or more leg portions 50 that extend or depend from the head-engaging section or body of the paddle. Referring to FIG. 1A, a cross-sectional side view of a paddle 22a is illustrated showing a leg portion 50 depending from a head-engaging portion or body 51 of the paddle. The leg portion 50 extends at an angle with respect to a plane 53 formed by body 51 of the paddle. In one embodiment, leg portion 50 extends generally approximately 45 degrees with respect to a plane 53 formed by paddle body 51. To accommodate and accept the leg portion or portion of the paddle, respective slots 56 are formed in the backboard proximate to each paddle and specifically proximate to the leg portions dependent therefrom (See FIG. 1). The number of slots may vary, as discussed below. For example, the embodiment illustrated in FIGS. 1 and 2 utilizes a pair of slots per paddle corresponding to the pair of leg portions depending from the paddles. The slots extend generally transverse to a longitudinal axis of the board.

Figure 1D:
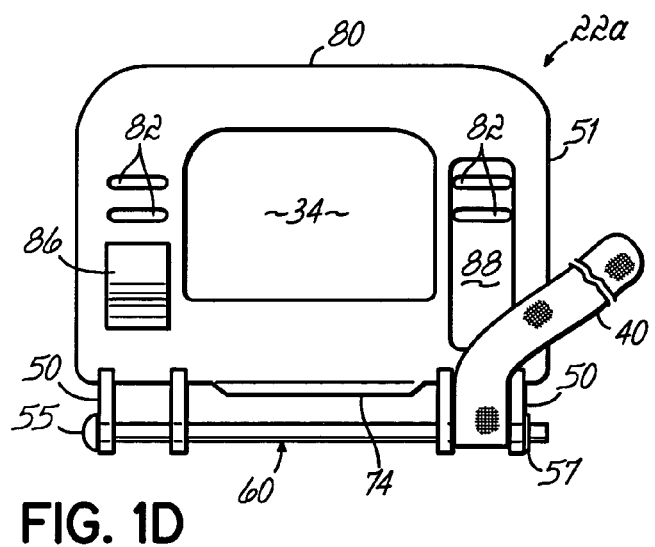
FIG. 1D is a perspective side view of an embodiment of a paddle of the invention.
Figure 1C:
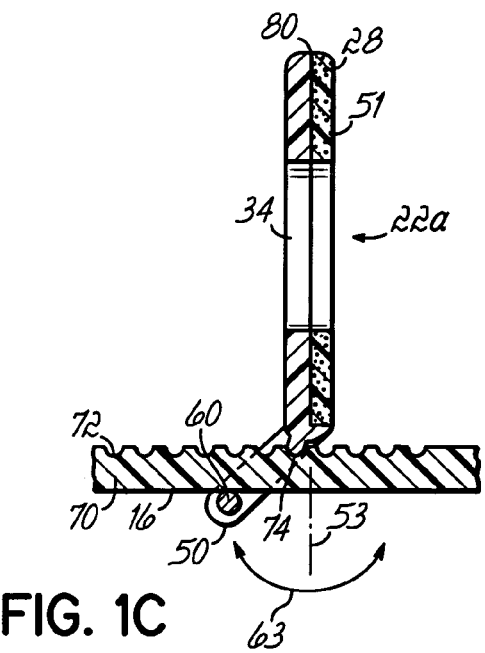
FIG. 1C is a side view, in cross-section similar to FIG. 1A, of a paddle in the support position.

Referring to FIG. 1D, two leg portions 50 are shown extending from paddle 22a. The paddles also include spanning portions 60 that depend from the leg portions and engage the backboard to secure the paddle with the backboard. In the embodiment illustrated in FIGS. 1, and 1A–1C, the spanning portion 60 of the paddle is in the form of a pin or dowel 60, which spans between the leg portions 50 of the paddle. In the embodiment of FIG. 1, the spanning portion 60 spans generally along the back side 16 of the backboard, securing the paddle to the backboard (See FIG. 8). Furthermore, as noted below, the spanning portion 60 prevents the various paddles from being over-rotated in the support position so that they continue to remain at their desired support angle (e.g. 90 degrees) and to support the head and neck of a patient even when the backboard is turned on its side.

The spanning portion 60 of the paddle, such as the dowel or pin illustrated in FIGS. 1A–1C, allows the paddle to be moved transversely on the backboard to space the paddles apart or to move them closer together to accommodate the patient. When the paddles are rotated upwardly from the storage position (FIG. 1A) and generally upwardly through a range of approximately 20 degrees to 70 degrees above the plane of the backboard (FIG. 1B), the paddle may slide freely transversely on the board as illustrated by arrows 62 in FIGS. 1A, 1B. As shown in FIG. 1C, when the paddle is moved to the support position, the spanning portion 60 engages the backboard, such as by engaging the back side 16 of the backboard, and along with other portions of the paddle, prevents the paddle from being over-rotated in the direction of arrow 64 significantly past a desirable support position, such as a generally perpendicular position. In one embodiment, it is desirable that the paddle is prevented from movement beyond approximately 20 degrees from the perpendicular or beyond approximately 110°. Of course, the paddles might be confined even closer to the perpendicular, like under approximately +10 degrees or +5 degrees from that position. The spanning portion is held into position by the leg portions 50 of the paddle, which have appropriate openings formed therein. That is, the dowel in the illustrated embodiment is a separate part slid into appropriate openings formed in the leg portions. The dowel has a head 55 (See FIGS. 1C, 8) to secure it at one end. The spanning portion or dowel is then locked into place by securing the other end of the dowel with clips or other structures 57 (See FIGS. 1C, 8). Alternatively, the spanning portion might be integrally formed with the leg portions of the paddle to span between the leg portions and secure the paddle with the backboard. Again, although two leg portions are shown for each paddle, a greater or lesser number of leg portions may be utilized with suitable spanning portions for engaging the backboard to secure the paddle to the backboard. As noted, spanning portion may be integral with the leg portions, such as being molded with the leg portions. In the embodiment of the paddle as illustrated in the Figures, the leg portions are generally molded or formed integral with the paddle which as being molded with the paddle. Alternatively, they might be separately formed similar to the spanning portion 60, then secured to the paddle body 51. Preferably, any securing structures such as screws or bolts, which couple portions of the paddle together, are x-ray translucent.

In accordance with one aspect of the invention, in order to provide the necessary clearance between the spanning portion 60 and the paddle body 51 for the purposes of movement of the paddles closer together or further apart, the spanning portion moves in a generally arcuate path between the storage and support positions. Referring to FIGS. 1A, 1B, and 1C, in the storage position, the spanning portion 60, such as the dowel, rests against the back side 16 of the backboard. Generally, friction, and the engagement of the paddle body 51 and spanning portion 60 against the sides of the backboard, prevents or hinders movement of the paddle laterally on the board when it is in a storage position and the backboard is stored. When the paddle is folded up or hinged up toward the support position, as illustrated in FIG. 1B, the spanning portion 60 travels a generally arcuate path away from the back side 16, and then again toward the back side 16 when the paddle is locked in the support position, as illustrated in FIG. 1C. That is, as illustrated in FIG. 1B, movement of the spanning portion along the generally arcuate path 63 moves the spanning portion 60 away from the back side 16 to allow for lateral movement of the paddles, such as in the direction of arrow 62. The spanning portion is disengaged from the backboard and the paddle is free to move or slide. Such generally arcuate movement of the spanning portion provides for easy adjustment of the paddles when they are between the storage and support positions. The arcuate path also ensures that the spanning portion subsequently engages the back side of the backboard to ensure that the paddles are held appropriately or locked in their storage and support positions. Usually, depending upon the positioning of the paddles, the spanning portions 60 will not take a purely arcuate path, as illustrated in FIG. 1B, because the paddles will also be moved laterally, once they are out of the storage position. For example, the spanning portion 60 might move arcuately to the position illustrated in FIG. 1B, and then might move in a linear fashion (arrow 62) as the paddles are adjusted to their proper widths for supporting the head and neck of a patient. Then, as the paddles are moved the rest of the way up to the storage position, as illustrated in FIG. 1C, a generally arcuate path might again be traversed by the spanning portion 60. Therefore, as used herein, the term "generally arcuate path" does not require that the arc be continuous, but only that the spanning portion move away from the back side of the backboard and then back toward that back side for movement between the storage and support positions.

Figure 8:
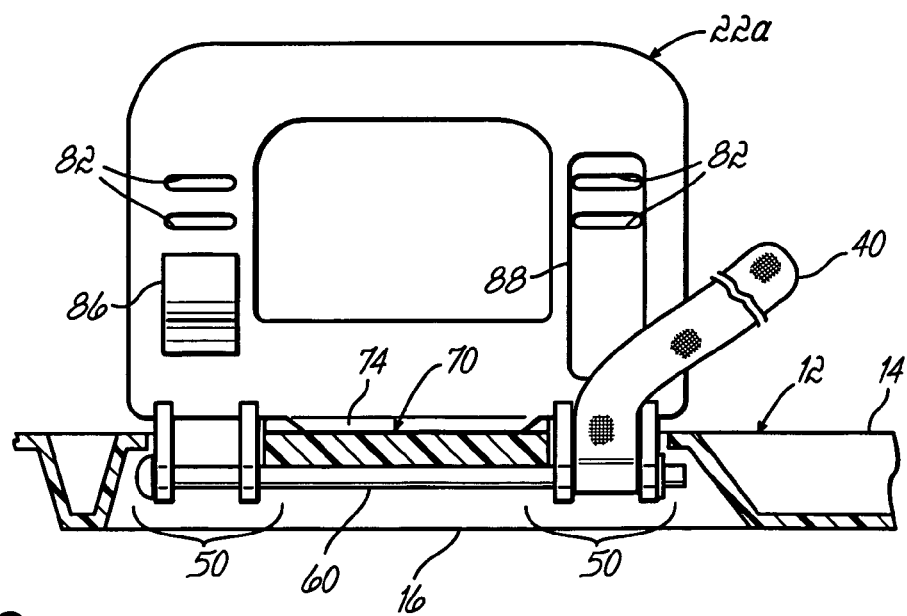
FIG. 8 is a side view, in partial cross-section, of a paddle of the invention in the support position.

Referring to FIG. 8, a side view of the paddle is shown, in partial cross-section, wherein the paddle is in the support position. As illustrated, the spanning portion 60 spans between the leg portions 50 and engages a portion of the backboard, such as the back side 16 of the backboard to secure the paddle and prevent the paddle from rotating in a storage position generally beyond perpendicular or some other desired angle. In accordance with one aspect of the present invention, the spanning portion engages the backboard when the paddle is moved to the support position and restricts movement of the paddle in the support position significantly beyond 90 degrees from the plane of the backboard. Preferably, in the illustrated embodiment, the spanning portion 60 maintains the paddle generally close to perpendicular. In that way, the neck and head of a patient are maintained in a desirable position on the backboard when the backboard is moved, and particularly when it is turned on its side. As may be appreciated, with the head secured between the paddles, such as with straps 40, turning the backboard 12 on its side, such as to move the patient between a doorway or some other opening, puts significant stress upon the upper portions of the paddle pair because the weight of the head cantilevers from that paddle. In the present invention, with the paddles prevented from rotating in the support position significantly beyond perpendicular or 90 degrees; this ensures that proper immobilization of the head and neck is maintained during movement of the patient. Generally, when the straps 40 are secured into position snugly on the head and neck of a patient, the paddles will be secured in a generally perpendicular position, ensuring full contact between the sides of the paddles and the head and neck of the patient. Proper utilization of the securement straps and proper positioning of the paddles on the sides of the head ensure that the paddles will generally not be less than approximately perpendicular or 90 degrees from the plane of the backboard.

In accordance with another aspect of the present invention, in the support position, the paddles are locked into position at the proper spacing, utilizing index structures that are engaged by the paddles. The paddles generally engage their respective index structures when the paddles are moved to the support position and thereby are locked relative to each other to support a patient's head and neck. Preferably, they are locked in a position that is centered about the center of the longitudinal axis of the backboard so that the patient's head and neck are centered on the backboard with the patient.

Referring to FIG. 1, index structures 70 are illustrated positioned on a front side of the backboard. The index structures 70 of FIG. 1 are in the form of a plurality of grooves (See FIG. 7), which extend longitudinally with respect to the backboard's long axis. The grooves 72 define various index points along the index structure for positioning of the paddles 22a, 22b. The grooves 72 may be formed as individual index structures for each paddle, as illustrated in the Figures. Alternatively, they may be part of a continuous index structure with a portion of the index structure being utilized for each respective paddle. The embodiment in FIG. 1 shows two individual index structures 70, one for each paddle. The index structures are positioned proximate a side of the slot or slots.

The index structures, such as grooves 72, may be integrally formed with the backboard 12, such as by being molded as part of the backboard. Alternatively, the index structure or structures might be separately formed and then secured to the backboard. For example, the grooves 72 might be formed in a plate that is then fastened to the backboard, such as with screws or other fasteners. While the grooves 72 are shown somewhat elongated to engage in an elongated, protruding ridge 74 of the paddles, as discussed below, they might be shortened to essentially form indents. The protruding ridge 74 would then be appropriately shortened to essentially form a knob to engage the indent and secure the transverse or lateral spacing of the paddles 22a, 22b.

To lock the paddles into position with respect to each other and to prevent them from being spread apart when the head and neck of the patient has been immobilized, a portion of the paddle engages the respective index structure. Specifically, in an embodiment illustrated in FIGS. 1 and 1A–1C, a protruding ridge 74 engages a respective groove 72 of the index structure 70. Referring to FIGS. 1A and 1B, when the paddle is moved from the storage position and is positioned generally in the range of 20 degrees to 70 degrees above the plane of the backboard, the spanning portion 60 and the ridge 74 of the paddle are not forced to engage the backboard and the grooves 72, respectively. That is, they are double open-ended grooves. In that way, the paddle slides freely in the direction of arrow 62 (see FIG. 1A) to the proper position, such as close to the neck and head of a patient lying on the backboard. At the proper position the paddle can be moved or rotated completely upwardly to the support position, which, for example, may be generally perpendicular to the plane of the backboard. At that time, the spanning structure 60 is forced into engagement with the backboard such as the back side 16 of the backboard, and the ridge 74 meets and slides into a particular groove 72 to lock the paddle at an index point on the index structure. As illustrated in the cross-section of FIG. 1B, the ridge 74 seats within the respective grove 72 when the paddle is in the support position. The engagement of the index structure by the paddle in that way laterally locks the position of the paddle so that it cannot be moved apart from the opposing paddle. With both the paddles in the support position and locked in such a way, the width or spacing between the opposing paddles for accommodating the head and neck of the patient is fixed. The present invention may accommodate a wide variety of head widths, ranging from pediatric to adult, even up to a patient with a helmet, such as a motorcycle helmet, on their head.

As illustrated in FIG. 1, the ridge 74 is dimensioned to generally span the length of the grooves of index structure 70 to provide proper securement of the paddles in the proper position. The spacing between the various index grooves 72 and the length of the grooves and the ridge 74 may be varied depending on the desired spacing of the indexing points and the robustness of the paddles and their securement. When the paddles are moved to the vertical or support position with respect to the backboard, the protruding ridges 74 are preferably configured to fit somewhat snugly into the grooves 72. This allows the paddles to freely stand up in a support position while simultaneously locking the transverse position of the paddles on the backboard. The straps 40 can then be applied to span the head and neck of the patient and between the opposing paddles as illustrated in FIG. 2.

In accordance with another aspect of the present invention, it is desirable that a backboard, particularly the head and neck restraining portion of such a backboard, be readily and easily cleanable. Prior art backboard and prior art head/neck immobilization structures have provided a plurality of cavities and recesses in which blood or other bodily fluids might collect when in use. To then clean and sanitize the structures for the next use, medical personnel must painstakingly scrub the structures and get into the various cavities to reduce the risk of transmission of fluid and blood-borne pathogens and contamination of a subsequent patient. In the present invention, the grooves 74 are open at their ends and open into the respective slots 45, as illustrated in FIGS. 1, 2, and 7. In that way, the grooves can be wiped clean without any corners or walls for catching fluids. That is, the contents of the grooves can be wiped into the slots 56 which are open and therefore subject to easy cleaning. Alternatively, a fluid such as water or a disinfectant can be sprayed down into the grooves and will easily flow out the open ends and into the slots 56, and thereby off the backboard.

Figure 6:
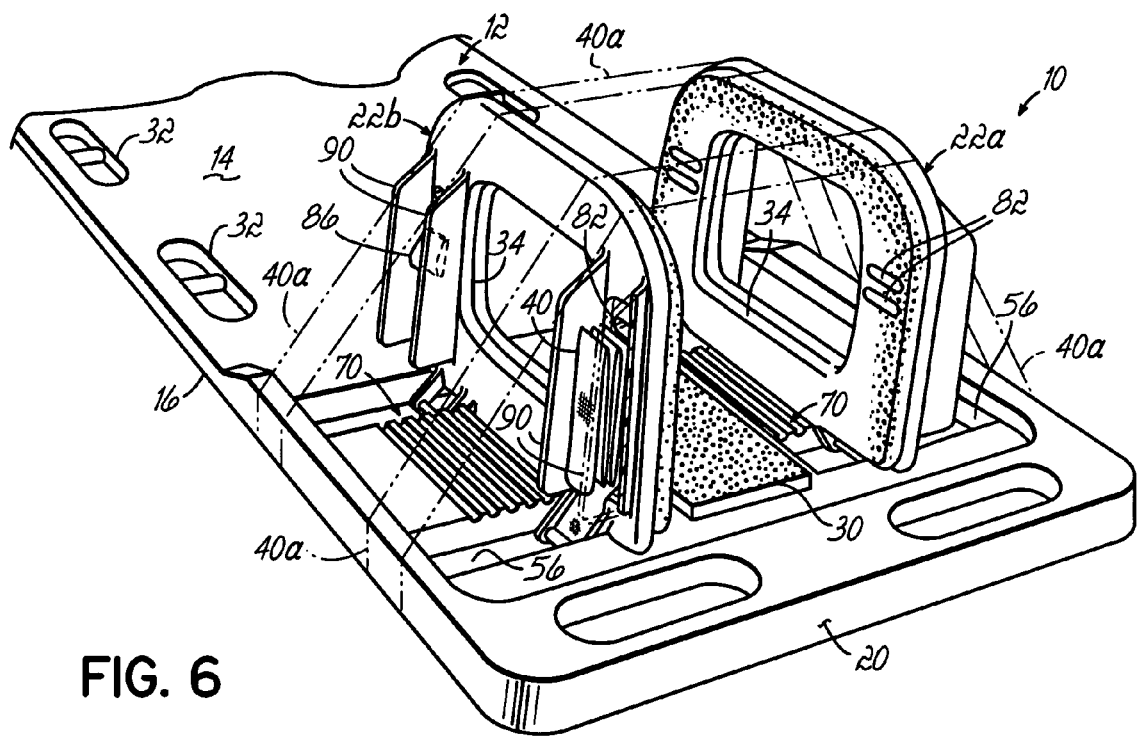
FIG. 6 is a perspective view of an alternative embodiment of the present invention.

To secure the paddles together in a support position to support a patient's head and neck, straps 40 may be utilized to span between the paddles and over a patient's head and neck, as illustrated in FIG. 2. Referring to FIG. 6, such straps may be made of tape 40a that span across the top edges of the paddle and are secured to the edges of the backboard in the typical securement methodology. However, by spanning tape across the top edges 80 of the paddle, the height of the securing straps or tape 40 is set by the height of the paddles. This may not provide desirable securement of the patient's head and neck, particularly for smaller patients such as infants and toddlers whose heads will be significantly below the height of the edges. In accordance with another aspect of the present invention, the strap 40 is adjustable in height on the paddle to adjust to different head height. Referring to FIGS. 1 and 2, openings 82 are formed in the paddles to receive the straps 40 at different heights on the paddle. Two such vertically spaced openings 82 are shown in the embodiment of the Figures. However a greater number of openings may be utilized for adjustment purposes. In that way, rather than spanning over the top edges 80 of the paddles, the straps 40 extend through the paddles and thereacross to span across the patient's head as illustrated in FIG. 2. The corresponding openings 82 are formed in each paddle for each strap utilized. In the illustrated embodiment, two straps are utilized, one at the forward end of the paddle (closest to the patient's forehead) and one at the rearward end of the paddle (closest to the patient's chin). The ends of the straps may be coupled to the backboard in any suitable fashion.

In the disclosed embodiments, a single strap is secured to each paddle and is secured with that paddle. The strap then spans across to the other paddle and is secured into position with an appropriate fastening technique. Referring to FIGS. 1 and 2, an end of the strap 40 is shown secured at a leg portion. Specifically, referring to FIG. 1C, the leg portions 50 are split into separate sections to allow the strap 40 to be secured around the spanning portion 60 that engages the leg portion 50, such as a dowel or pin. For example, the strap end might be slid around the dowel and be sewn. For immobilizing the head and neck, the free end of the strap is placed through the desired openings 82 in the paddles, over the head and neck of the patient, and through similar openings in the other paddles. As illustrated in FIG. 2, multiple straps, one on the forehead, and one proximate to the chin, might be utilized. The free end of the strap is then secured with an appropriate method, such as with adhesives, a buckle, hook/loop fasteners, or other securing mechanisms. In the illustrated embodiment, a cam buckle 86 is utilized to receive the free end of the strap 40.

Therefore, in accordance with one aspect of the present invention, the strap is integral with the immobilization device 10 and is stored with the backboard along with the paddles 22a, 22b to be readily available for use. Therefore, precious time is not wasted in securing paddles or blocks to the board and then securing the head between the paddles and block such as with separate tape or strap structures. While the straps 40 are shown secured to opposite paddles, they might be fixed to the same paddle with both free ends extending over to the other paddle.

The present invention contemplates storage of the straps with the paddles in the storage position. In accordance with another aspect of the present invention, the paddles are configured for storing the straps out of the way when the paddles are in the storage position. In one embodiment, as illustrated in FIGS. 1, 2, and 3, an indent 88 is formed in the back of the paddle for receiving a folded strap. When the paddle is then folded to the storage position, an interference fit keeps it within the paddle to keep it out of the way to prevent it from being caught during storage of the immobilization device 10. Alternatively, as illustrated in FIG. 6, raised walls 90 might be utilized to capture the strap 40 to secure it in an interference fit when the paddles are in a storage position. Therefore, once the strap is folded and loaded into the paddle, it is prevented from becoming loose by a tight interference fit.

An alternative embodiment of the invention is illustrated in FIG. 3. Layers 28 utilized with the paddles 22a, 22b may be removable for being disposable, or disinfected and reused. For example, they might be fastened by a suitable adhesive or hook/loop fasteners to be readily pulled away from the paddles after each use and discarded. Alternatively, they might slide into tracks or otherwise engage paddles 22a, 22b to be easily removed and replaced after each use so that the layer does not need to be cleaned. Referring to FIG. 13, if the paddle is split, a suitably split cushion is utilized to allow the separate sections of the paddle to be separated as desired.

FIGS. 4 and 5 illustrate another aspect and embodiment of the present invention, which facilitates grasping and lifting the backboard by medical personnel, and also ensures sufficient operation of the paddles when they are adjusted. Referring to FIG. 4, the backboard 12 includes a network of raised areas 92 along the length of the backboard and also proximate the head end 20 of the backboard. The raised areas elevate the hand holes 32 off the ground to allow medical personnel to easily slide their hands underneath the backboard to lift a patient secured thereon. Generally, the hand holes 32 will be placed equidistant along the border of the backboard 12 to promote balance while carrying the patient. The raised areas might be formed by securing appropriate ridges to the back side of the backboard. Alternatively, such raised areas may be molded with the backboard, such as when the backboard is made out of a suitable plastic material. In accordance with another aspect of the invention as illustrated in FIG. 4, the hand holes 32 might include pins that span the holes and are configured for strapping to clips or straps such as for strapping a patient onto the backboard.

The raised areas 92 proximate the head end 21 provide proper clearance for movement of the leg portions 50 and spanning portion 60 of the paddles. Turning again to FIGS. 1A, 1B, clearance for the lateral adjustment of the paddles is necessary so that the leg portions and spanning portion are not hindered. Similarly, interference between the paddle and a ground or support surface is prevented so the paddles may be readily moved between storage and support positions.

Figure 9:
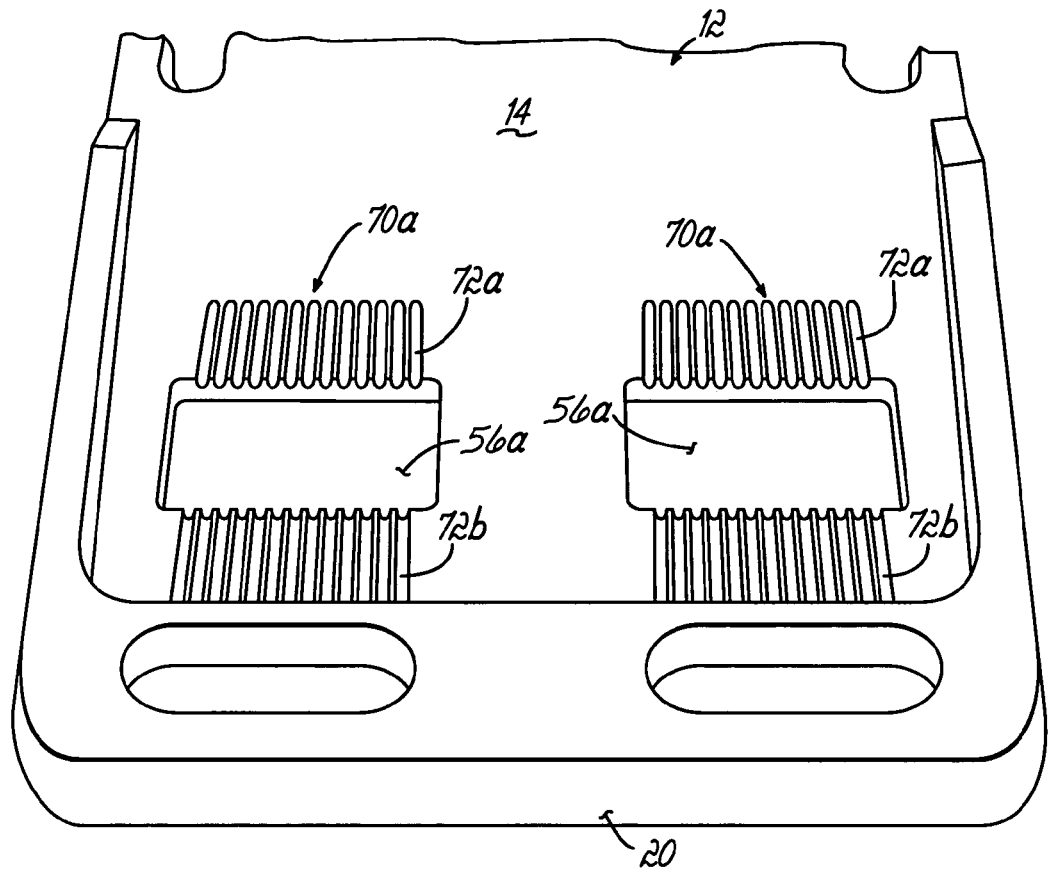
FIG. 9 is a perspective view of an alternative embodiment of the present invention.
Figure 10:
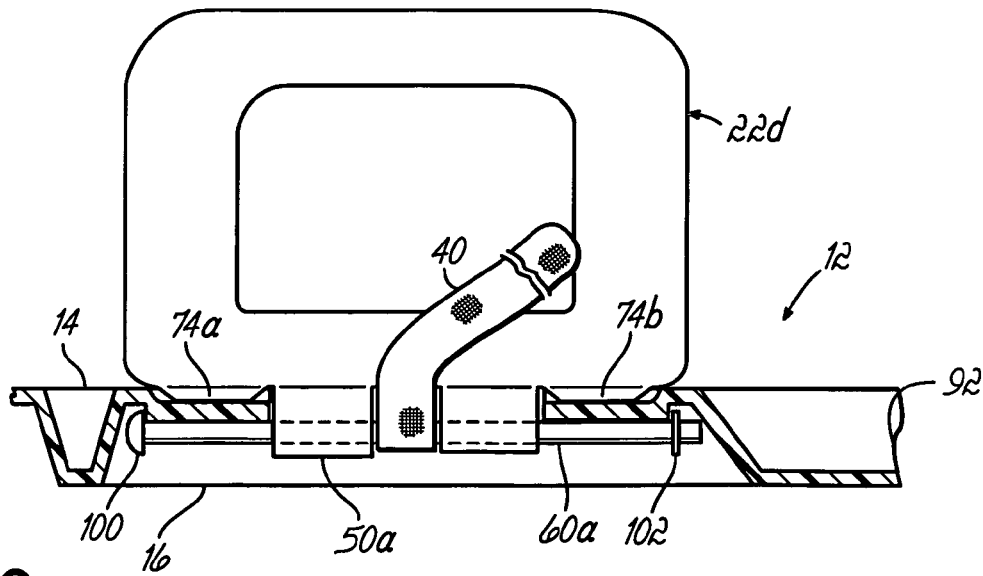
FIG. 10 is a side view, in partial cross-section, of an alternative embodiment of the invention illustrating the paddle in the support position.

FIGS. 9 and 10 illustrate an alternative embodiment of the invention, in which a single slot 56a is utilized rather than multiple slots, while the index structure is in the form of a plurality of grooves 72a, 72b positioned on either side of the slot 56a. That is, the index structures 70a, rather than spanning between two slots, is positioned on either side of the single slot 56a. FIG. 10 illustrates a paddle 22d that engages slot 56a and the index structure 70a. The protruding ridge is divided into two sections 74a and 74b, for engaging the respective grooves 72a and 72b in the index structure when the paddle 22d is moved to the support position as illustrated in FIG. 10. Paddle 22d includes a single leg portion 50a that engages the slot 56a. The spanning portion 60a of the paddle 22d spans to either side of a leg portion 50a to secure the paddle to the backboard. In the embodiment illustrated in FIG. 10, the spanning portion is in the form of a pin or a dowel that extends through an appropriate opening formed in the leg portion 50a and spans along a back side of the board generally below the grooves 72a, 72b of the index structure. The pin or dowel is held into position on one side by a head 100 and on the other side by a clip 102. Alternatively, as noted above, the spanning portion might be integrally formed with the leg portion 50 or the paddle 22d, such as by being molded with either of those components.

Figure 11:
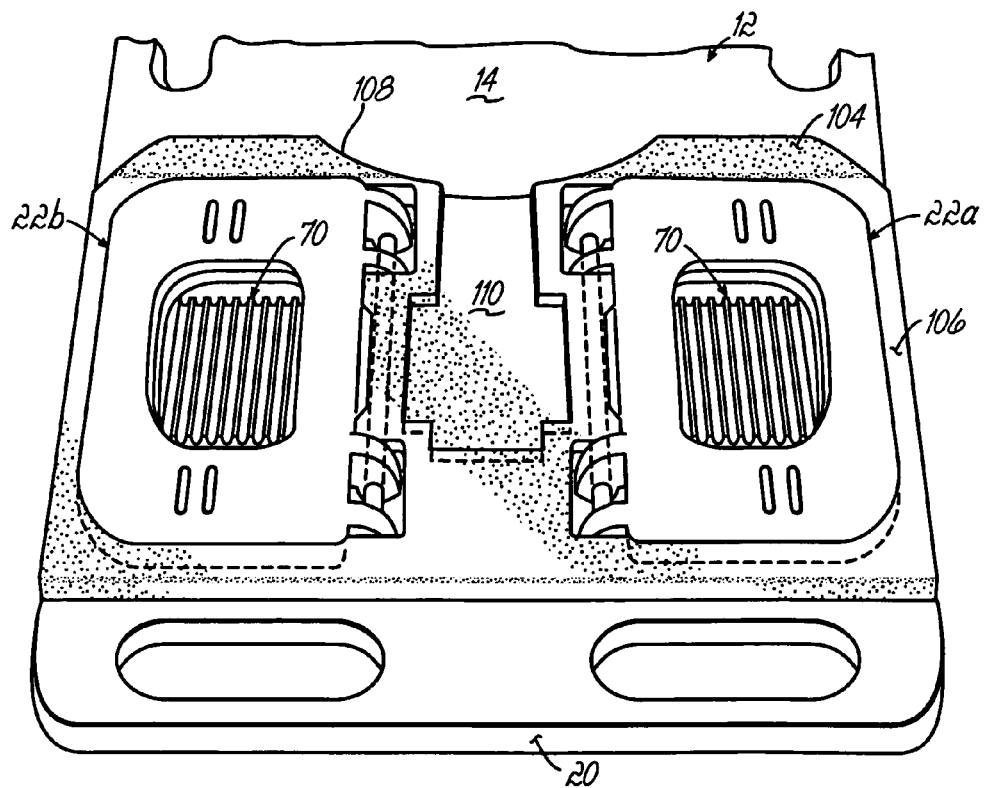
FIG. 11 is a perspective view of an alternative embodiment of the present invention with paddles in the storage position.

FIG. 11 illustrates an alternative head end for an immobilization device of the present invention. The paddles utilized are similar to those illustrated in FIG. 1, although they could be any suitable paddles, included those illustrated herein. The head end 20 of the backboard in FIG. 11 utilizes a raised area 104 that has recessed areas therein 106 for receiving the paddles 22a, 22b in the storage position. The raised area tapers at a rearward edge 108 down to the front side of the backboard. In that way, the raised area 104 defines an area for supporting the head of a patient and also demarcates a position at the rearward edge 108 for positioning the shoulders of a patient. That is, at the tapered demarcation provided at the rearward edge 108, the medical personnel have a reference point for sliding the patient's body along the board for proper alignment of their head with the paddles. Because of different physiologies among patients, the edge 108 does not provide an exact point, but rather offers a reference point between the paddles. To receive the head, an indent portion 110 is formed to allow the head to nest between the paddles 22a, 22b. The raised portion might be formed as a separate piece attached to the front side 14 of the boarded or it might be molded integrally with the board. The indent portion 110 in one embodiment includes a suitable cushion material, similar to cushion 30, as illustrated in FIG. 1.

Figure 12:
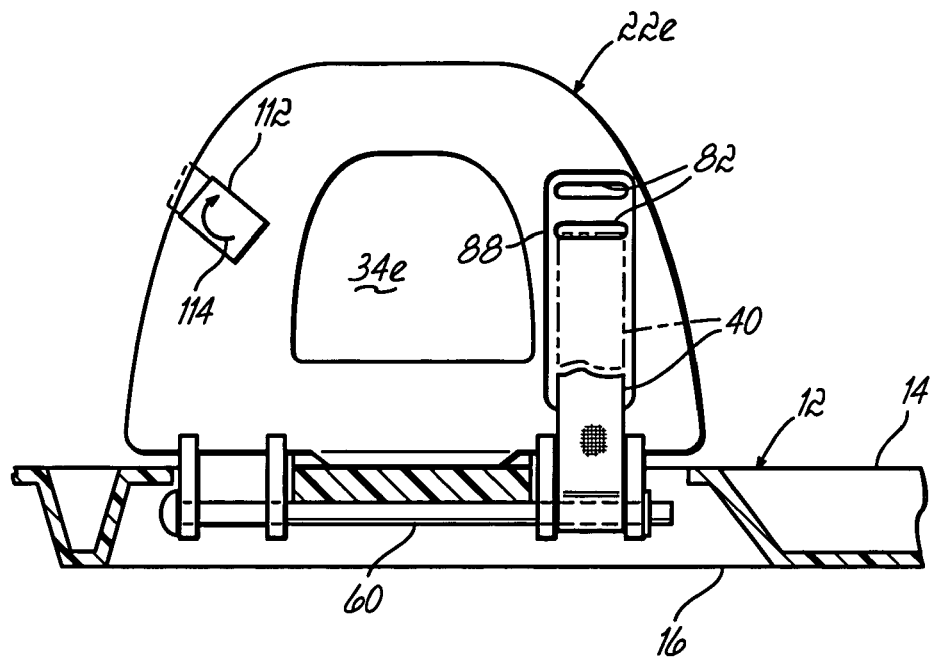
FIG. 12 is a side view, in partial cross-section, of an alternative paddle of the present invention.

FIG. 12 illustrates an alternative embodiment of a paddle 22e in which the height of the paddle is raised to provide a wider and taller ear hole 34e. Paddle 22e is configured to have an indent area 88 therein for storing the strap 40. Furthermore, the paddle has openings 82 for positioning of the strap along the height of the paddle to adjust to different patient heads. To receive the free end of the strap 40, such as from the other paddle, a buckle, such as a cam buckle 112 or other attachment device is utilized and is rotatable about a center axis as illustrated by arrow 114. The other end of strap 40 is secured, such as by coupling with spanning portion 60.

FIGS. 14–17 illustrate further alternative embodiments of the invention, and particularly illustrate an alternative index structure for locking the paddles at certain indexed positions on the backboard. Rather than being positioned on the front side of the backboard, the index structure is incorporated into slots formed through the backboard. Specifically, with respect to FIG. 14, a paddle 22f is shown and is somewhat similar to other paddles discussed previously, such as those shown in FIGS. 7 and 8. Therefore, like numerals are utilized where possible for similar components between the embodiments.

Figure 16:
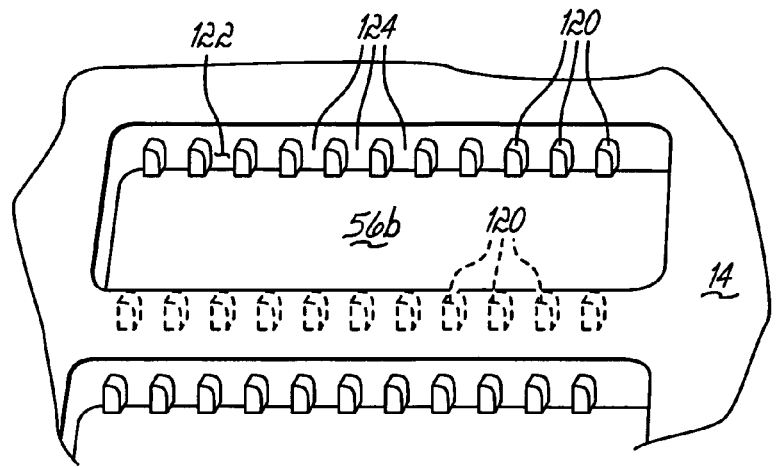
FIG. 16 is a partial cut-away perspective view of an alternative index structure of the present invention.

The index structure 70b includes a plurality of posts 120 that extend into slots 56b formed in the backboard. As illustrated in FIG. 16, two sets of posts in an opposing relationship extend into the slots 56b from a side wall 122 of the slots. The posts provide index channels 124 there between into which corresponding index tabs 126 slide when the paddles 22f are in the support position (see FIG. 14). Therefore, the posts 120 provide an index structure 70b for indexing the paddle 22f at desired positions to provide for proper spacing between the opposing paddles to secure and immobilize the head and neck of a patient. Similar to the paddles discussed above, the paddle may be freely movable when raised to a position between the storage position and the support position and will slide transversely with respect to the slots 56b to vary the space between the opposing paddles. When the paddles are moved to a generally perpendicular support position and the spanning portion 60 of the paddle engages the backboard, the index tabs 126 engage the index posts 120 in the slots 156b. More particularly, the index tabs 126 slide into the channels 124 created between the index posts. The embodiments illustrated in FIGS. 14–17 further enhance the cleanability of the immobilization device of the invention by eliminating any cavity that catches fluid. Any fluid proximate to slots 56b and the paddles 22f and specifically fluid contacting the index structures 70b will be able to pass over the slots and various posts 120 that form the open channels 124. In that way, water or other fluid may be directed down through the channels 124 and around the posts to keep them clean of blood or other bodily fluids.

Figure 17:
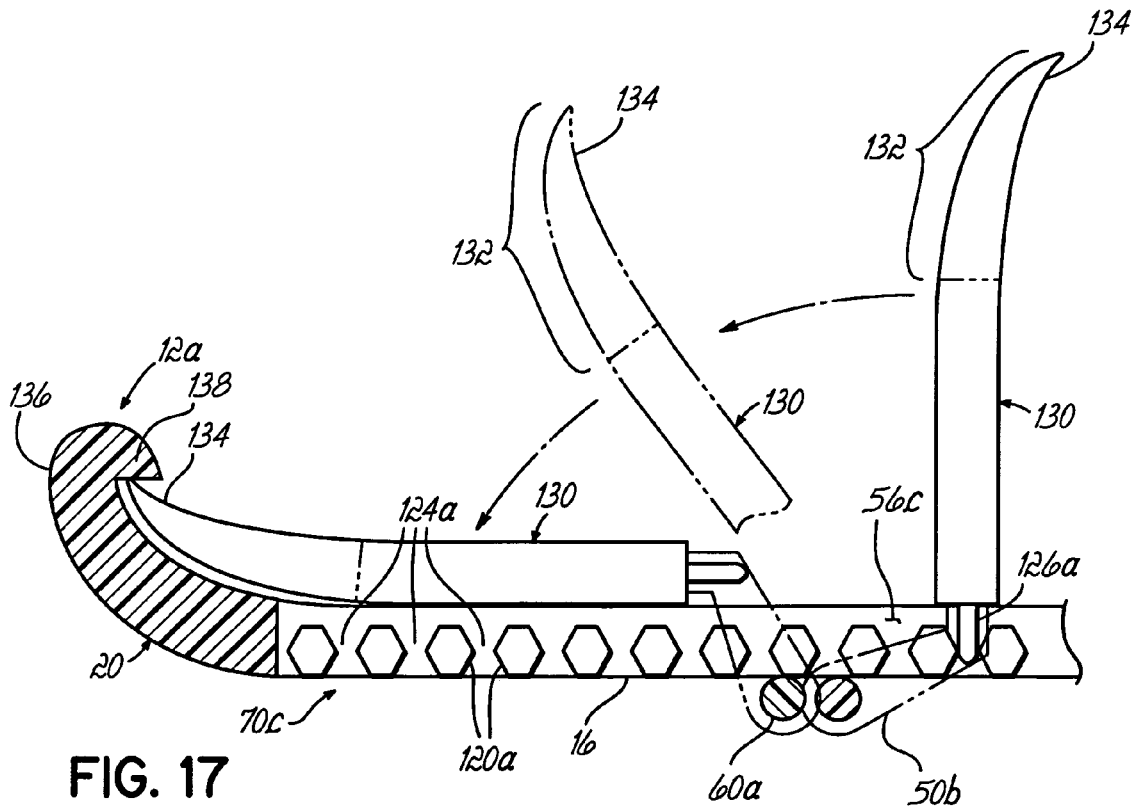
FIG. 17 is a partial cross-sectional view of an alternative embodiment of the invention.

FIG. 17 illustrates another alternative embodiment of the invention and shows a cross-sectional view of a backboard and paddle shaped for more closely conforming to the head of a patient. Specifically, paddle 130 is not generally similar to other paddles discussed herein above. Rather, the paddle has a concave shape toward the head and neck of a patient to provide better conformity around the head of the patient. The top 132 of the paddle 130 has a concave shape that will more closely conform to the side of the head of a patient. Paddle 130 may be made of a pliable material such as a plastic or hard rubber material that will allow it to more closely conform to a patient's head when in the support position. Straps, tape or other securing structures spanning between the opposing paddles 130 will secure the paddles in the support position and will more closely conform the paddles to the patient's head and neck. In one embodiment, the entire paddle may be formed of pliable material. Alternatively, the paddle might include a pliable tip section 134 that will provide conformity generally where the paddle engages curved portions on the side of a patient's head or neck. In another aspect of the invention, as shown in FIG. 17, the side of the backboard, proximate the head end 20 where the paddles are located, is formed to hold the conformable paddles 130 in the storage position. As illustrated in FIG. 17, the backboard 12a includes a side section 136 with an overhang 138 that captures the top portion 134 of the paddle. The compliant paddle may then be pulled from a storage position and out from the overhang 138 to be moved to the support position as illustrated in FIG. 17. Paddle 130 includes one or more leg portions 50b, which extends through slots 56c formed in the backboard. A spanning portion 60a secures the paddle 130 with the backboard and provides a stop mechanism for the paddle in the support position to prevent over-rotation, as discussed above. In the embodiment of FIG. 17, an index structure 70c includes a plurality of posts 120a at index positions along the width of the board. Index tabs 126a on the paddles 130 engage channels 120a formed between the index posts 120a to laterally or transversely secure the paddle in a specific indexed position corresponding to a particular width of the head and neck of a patient. The embodiment of FIG. 17 also provides the benefit of open channels 124a that do not collect bodily fluids and associated blood/fluid-borne pathogens. The paddles 130 may be secured around the head and neck of a patient such as with straps, tapes, or other securement structures. Furthermore, the paddles 130 may have other features such as ear holes and strap storage components similar to those in the embodiments discussed above.

Figure 18:
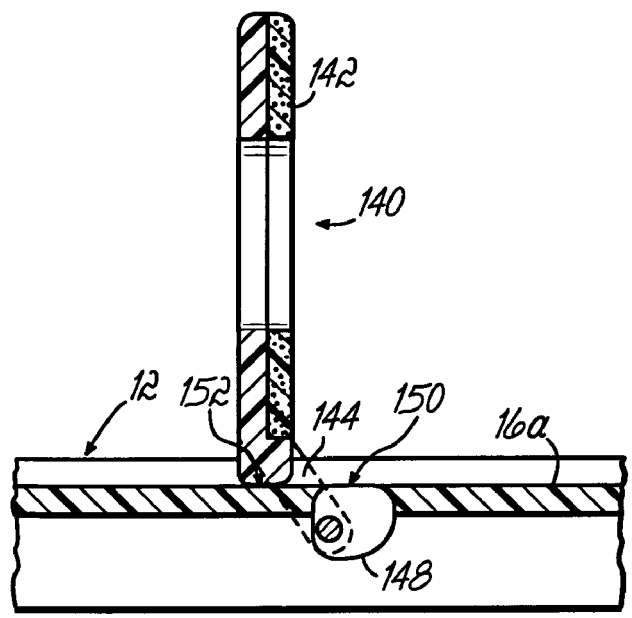
FIG. 18 is an end cross-sectional view of another embodiment of the invention.
Figure 19:
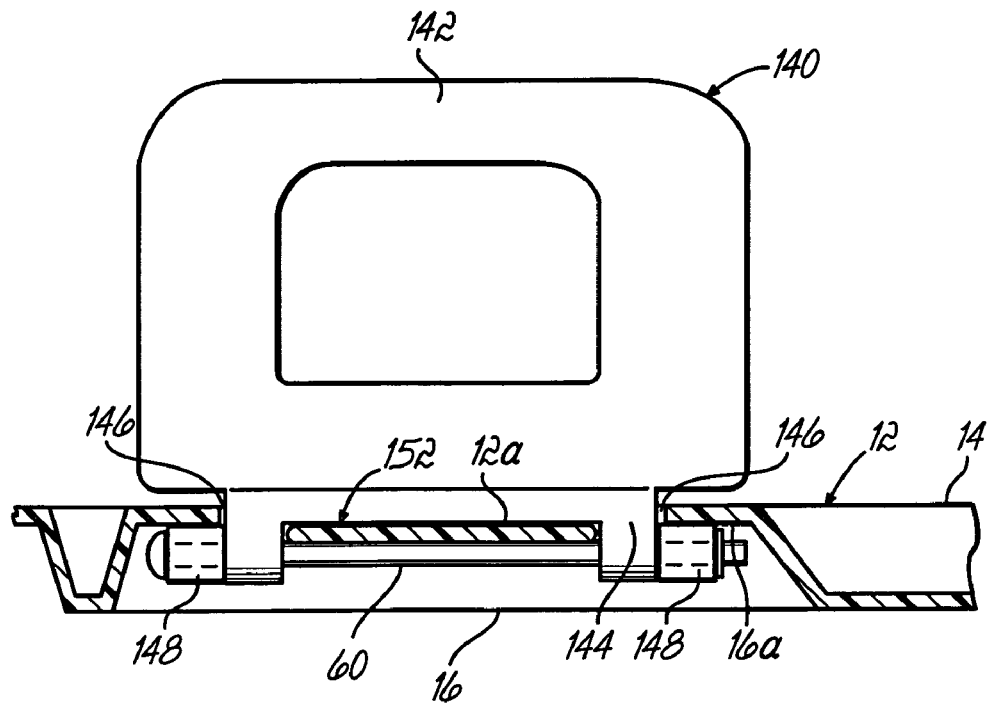
FIG. 19 is a side cross-sectional view of the embodiment in FIG. 18.

In an alternative embodiment of the invention, as illustrated in FIGS. 18 and 19, a specific index structure with discrete index positions, is not utilized to hold the paddle in position when it is moved to the support position. Rather, a friction fit between elements of the paddle and the backboard provides the fixation of the paddle in a specific position. More specifically, the spanning portion and paddle body rest against respective back side and front side surfaces to secure the paddle in place in the support position. Referring to FIG. 18, paddle 140 has a paddle body 142 that moves between a support position and a storage position, as discussed above. One or more leg portions 144 depend from the paddle body and extend through respective slots 146 formed in the backboard. A spanning portion 60, such as a dowel, spans from the leg portion or spans between and is secured by the leg portions 144. In one embodiment, the spanning portion and paddle may be configured to pinch the backboard there between when the paddle is moved to the support position. That is, no index structure is utilized and the friction provided at the front and back sides of the backboard will hold the paddle in place. Alternatively, cam structures might be used as illustrated in FIGS. 18, 19. Positioned on the spanning portion 60 are one or more cams 148, which are configured to engage a back side 16 or a portion of the backboard to lock the paddle when it is in the support position, as illustrated in FIGS. 18 and 19. In the embodiment illustrated in the Figures, two cams 148 are utilized, one associated with each of the leg portions 144 extending through the backboard. Referring to FIG. 18, when the paddle 142 is moved to the support position, the cam 148 includes a flat surface 150, which engages a back side surface 16a of a portion of the backboard. Simultaneously, a portion of the paddle 152 engages a front side section 12a of the backboard. The cam 148 rolls about its pivot axis, which is generally co-axial with the dowel 60 to pinch itself and the paddle against respective surfaces of the backboard. For example, the surface 150 of cam 148 is directed against surface 16a, while the paddle is directed against surface 12a. The pinching provides a frictional engagement or interference with the backboard, such that the paddle is locked into the support position, as desired for supporting the head and neck of a patient. One advantage of the embodiment illustrated in FIGS. 18 and 19 is that discrete index positions are not utilized. Rather, the paddles may be adjusted to a seemingly infinite number of different head widths along the continuous respective backboard surfaces 12a, 16a. The cam 148 provides a wedging or pinching action in the support position; however, when the paddle is moved from the support position toward the storage position, the cam is free to pivot such that the flat surface 150 disengages from surface 16a to allow lateral movement of the paddle to a desired position.

FIG. 20 illustrates another embodiment of the present invention wherein the index structure 70 is utilized on the back side 16 of the board. Referring to FIG. 20, similar reference numerals are utilized to note similar elements. The index structure 70a utilizes grooves 72a at various index points along the index structure. The spanning portion 60, such as a dowel, and the grooves 72a are configured such that the dowel can engage the grooves when the dowel is moved to the support position, as illustrated in FIG. 20. A bottom surface of the paddle 74a engages surface 16 of the backboard, and the paddle is thereby locked into position.

While the present invention has been illustrated by a description of various embodiments and while these embodiments have been described in considerable detail, it is not the intention of the applicant to restrict or in any way limit the scope of the appended claims to such detail. For example, various features are shown for the different embodiments, but those features do not have to all be used on a single device. Different combinations of features and components might be used on various different embodiments of the immobilization device. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A patient immobilization device comprising:
   a backboard having a front side and a back side;
   a pair of opposing paddles slidably mounted on the backboard and configured, in a support position, to support the head of a patient;
   a securement strap fixed at one end with a paddle and configured to span between the paddles in the support position and secure a patient's head between the paddles;
   at least one opening formed in at least one of the paddles along the height of the paddle, the opening configured to receive the strap for spanning the securement strap between the opposing paddles at various heights in the paddle.

2. A patient immobilization device comprising:

a backboard having a front side and a back side;

a pair of opposing paddles slidably mounted on the backboard and configured to rotate between a storage position and generally up to a support position, to support the head of a patient;

at least one securing structure spanning between the opposing paddles to hold the paddles in the support position;

the paddles being flexible along their height such that a portion of the paddles will flex to rotate past the support position under the force of the securing structure to closely conform to the head and neck of a patient on the board.

3. The device of claim 2 wherein the top of the paddles are flexible for conforming to a patient.

4. A patient immobilization device comprising:

a backboard having a front side and a back side;

a pair of opposing paddles slidably mounted on the backboard and configured, in a support position, to support the head of a patient;

each paddle having multiple sections, wherein one section is moveable to a storage position to expose a portion of the head and/or neck while the other section remains in a support position to support the head and/or neck.

5. The device of claim 4 wherein the paddle includes a coupling structure for coupling the paddle sections together into a unitary paddle structure.

* * * * *